(12) United States Patent
Ton et al.

(10) Patent No.: US 7,771,463 B2
(45) Date of Patent: Aug. 10, 2010

(54) TWIST-DOWN IMPLANT DELIVERY TECHNOLOGIES

(76) Inventors: Dai T. Ton, 1514 Mt. Diablo Ave., Milpitas, CA (US) 95035; William R. George, 435 Oxford Way, Santa Cruz, CA (US) 95060; David Licata, P.O. Box 60819, Palo Alto, CA (US) 94306

( * ) Notice: Subject to any disclaimer, the term of this patent is extended or adjusted under 35 U.S.C. 154(b) by 947 days.

(21) Appl. No.: 11/266,587

(22) Filed: Nov. 2, 2005

(65) Prior Publication Data

US 2006/0111771 A1    May 25, 2006

Related U.S. Application Data

(63) Continuation-in-part of application No. 10/550,707, filed as application No. PCT/US2004/008909 on Mar. 23, 2004, and a continuation-in-part of application No. 10/745,778, filed on Dec. 24, 2003, and a continuation-in-part of application No. 10/746,452, filed on Dec. 24, 2003, and a continuation-in-part of application No. 10/746,455, filed on Dec. 24, 2003, which is a continuation-in-part of application No. 10/792,684, filed on Mar. 2, 2004, now abandoned.

(60) Provisional application No. 60/458,323, filed on Mar. 26, 2003, provisional application No. 60/462,219, filed on Apr. 10, 2003.

(51) Int. Cl.
    *A61F 2/06* (2006.01)
(52) U.S. Cl. ...................................... 623/1.11; 623/1.15
(58) Field of Classification Search ....... 623/1.11–1.15, 623/1.17, 1.2, 1.22–1.23, 1.3, 1.36, 1.5–1.54
    See application file for complete search history.

(56) References Cited

U.S. PATENT DOCUMENTS

| 4,503,569 A | 3/1985 | Dotter |
| 4,512,338 A | 4/1985 | Balko et al. |
| 4,553,545 A | 11/1985 | Maass et al. |
| 4,562,596 A | 1/1986 | Kornberg |

(Continued)

FOREIGN PATENT DOCUMENTS

DE           4420142       12/1995

(Continued)

OTHER PUBLICATIONS

Kandzari et al. "Clinical and Angiographic Efficacy of a Self-Expanding Nitinol Stent in Saphenous Vein Graft Athersclerotic Disease" Am. Heart J 145(5):868-874 (2003).
Rieu et al., "Radial Force of Coronary Stents: A Comparative Analysis" Catheterization and Cardiovascular Interventions 46:380-391(1999).
Supplementary European Search Report of EP Application No. 04758233, mailed Nov. 7, 2007, 7 pages total.

(Continued)

*Primary Examiner*—Todd E Manahan
*Assistant Examiner*—Erin Colello
(74) *Attorney, Agent, or Firm*—Townsend and Townsend and Crew LLP

(57) ABSTRACT

Medical devices and methods for delivery or implantation of tubular prostheses within hollow body organs and vessels or other luminal anatomy are disclosed. A prosthesis is held in a compressed from upon an inner wire of a delivery guide by twisting the device. The subject technologies may be used in the treatment of atherosclerosis in stenting procedures or for other purposes.

70 Claims, 19 Drawing Sheets

U.S. PATENT DOCUMENTS

| | | |
|---|---|---|
| 4,580,568 A | 4/1986 | Gianturco |
| 4,655,771 A | 4/1987 | Wallsten |
| 4,665,918 A | 5/1987 | Garza et al. |
| 4,732,152 A | 3/1988 | Wallsten et al. |
| 4,733,665 A | 3/1988 | Palmaz |
| 4,762,128 A | 8/1988 | Rosenbluth |
| 4,768,507 A * | 9/1988 | Fischell et al. ............. 623/1.11 |
| 4,771,773 A | 9/1988 | Kropf |
| 4,776,337 A | 10/1988 | Palmaz |
| 4,830,003 A | 5/1989 | Wolff et al. |
| 4,848,343 A | 7/1989 | Wallsten et al. |
| 4,875,480 A | 10/1989 | Imbert |
| 4,878,906 A | 11/1989 | Lindemann et al. |
| 4,893,623 A | 1/1990 | Rosenbluth |
| 4,913,141 A | 4/1990 | Hillstead |
| 4,950,227 A | 8/1990 | Savin et al. |
| 4,954,126 A | 9/1990 | Wallsten |
| 4,969,890 A | 11/1990 | Sugita et al. |
| 4,990,151 A | 2/1991 | Wallsten |
| 4,990,155 A | 2/1991 | Wilkoff |
| 4,998,539 A | 3/1991 | Delsanti |
| 5,019,085 A | 5/1991 | Hillstead |
| 5,019,090 A | 5/1991 | Pinchuk |
| 5,026,377 A | 6/1991 | Burton et al. |
| 5,035,706 A | 7/1991 | Giantureo et al. |
| 5,061,275 A | 10/1991 | Wallsten et al. |
| 5,064,435 A | 11/1991 | Porter |
| 5,067,957 A | 11/1991 | Jervis |
| 5,071,407 A | 12/1991 | Termin et al. |
| 5,089,006 A | 2/1992 | Stiles |
| 5,092,877 A | 3/1992 | Pinchuk |
| 5,102,417 A | 4/1992 | Palmaz |
| 5,108,407 A | 4/1992 | Geremia et al. |
| 5,108,416 A | 4/1992 | Ryan et al. |
| 5,122,136 A | 6/1992 | Guglielmi et al. |
| 5,147,370 A * | 9/1992 | McNamara et al. ........ 623/1.11 |
| 5,158,548 A | 10/1992 | Lau et al. |
| 5,160,341 A | 11/1992 | Brenneman et al. |
| 5,180,367 A | 1/1993 | Kontos et al. |
| 5,192,297 A | 3/1993 | Hull |
| 5,201,757 A | 4/1993 | Heyn et al. |
| 5,221,261 A | 6/1993 | Termin et al. |
| 5,242,399 A | 9/1993 | Lau et al. |
| 5,242,452 A | 9/1993 | Inoue |
| 5,246,445 A | 9/1993 | Yachia et al. |
| 5,263,964 A | 11/1993 | Purdy |
| 5,266,073 A | 11/1993 | Wall |
| 5,290,305 A | 3/1994 | Inoue |
| 5,306,294 A | 4/1994 | Winston et al. |
| 5,320,635 A | 6/1994 | Smith |
| 5,334,210 A | 8/1994 | Gianturco |
| 5,354,295 A | 10/1994 | Guglielmi et al. |
| 5,360,401 A | 11/1994 | Turnland et al. |
| 5,372,600 A | 12/1994 | Beyar et al. |
| 5,382,259 A | 1/1995 | Phelps et al. |
| 5,407,432 A | 4/1995 | Solar |
| 5,415,664 A | 5/1995 | Pinchuk |
| 5,423,829 A | 6/1995 | Pham et al. |
| 5,433,723 A | 7/1995 | Lindenberg et al. |
| 5,443,477 A | 8/1995 | Marin et al. |
| 5,445,646 A | 8/1995 | Euteneuer et al. |
| 5,476,505 A * | 12/1995 | Limon ....................... 623/1.11 |
| 5,484,444 A | 1/1996 | Braunschweiler et al. |
| 5,486,195 A | 1/1996 | Myers et al. |
| 5,507,771 A | 4/1996 | Gianturco |
| 5,522,836 A | 6/1996 | Palermo |
| 5,522,883 A | 6/1996 | Slater et al. |
| 5,534,007 A | 7/1996 | St. Germain et al. |
| 5,540,680 A | 7/1996 | Guglielmi et al. |
| 5,554,181 A | 9/1996 | Das |
| 5,569,245 A | 10/1996 | Guglielmi et al. |
| 5,571,135 A | 11/1996 | Fraser et al. |
| 5,578,074 A | 11/1996 | Mirigian |
| 5,591,196 A | 1/1997 | Marin et al. |
| 5,601,600 A | 2/1997 | Ton |
| 5,618,300 A | 4/1997 | Marin et al. |
| 5,634,928 A | 6/1997 | Fischell et al. |
| 5,639,274 A | 6/1997 | Fischell et al. |
| 5,643,254 A | 7/1997 | Scheldrup et al. |
| 5,653,748 A | 8/1997 | Strecker |
| 5,683,451 A | 11/1997 | Lenker et al. |
| 5,690,643 A | 11/1997 | Wijay |
| 5,690,644 A | 11/1997 | Yurek et al. |
| 5,702,364 A | 12/1997 | Euteneuer et al. |
| 5,702,418 A | 12/1997 | Ravenscroft |
| 5,725,549 A * | 3/1998 | Lam ........................ 623/1.15 |
| 5,725,551 A | 3/1998 | Myers et al. |
| 5,733,267 A | 3/1998 | Del Toro |
| 5,733,325 A | 3/1998 | Robinson et al. |
| 5,772,609 A | 6/1998 | Nguyen et al. |
| 5,772,668 A * | 6/1998 | Summers et al. ........... 623/1.11 |
| 5,772,669 A | 6/1998 | Vrba |
| 5,776,141 A | 7/1998 | Klein et al. |
| 5,776,142 A | 7/1998 | Gunderson |
| 5,782,838 A | 7/1998 | Beyar et al. |
| 5,788,707 A | 8/1998 | Del Toro et al. |
| 5,797,857 A | 8/1998 | Obitsu |
| 5,797,952 A | 8/1998 | Klein |
| 5,800,455 A | 9/1998 | Palermo et al. |
| 5,800,517 A | 9/1998 | Anderson et al. |
| 5,807,398 A | 9/1998 | Shaknovich |
| 5,810,837 A | 9/1998 | Hofmann et al. |
| 5,817,101 A | 10/1998 | Fiedler |
| 5,824,041 A * | 10/1998 | Lenker et al. ................ 606/195 |
| 5,824,053 A * | 10/1998 | Khosravi et al. ........... 623/1.15 |
| 5,824,054 A | 10/1998 | Khosravi et al. |
| 5,824,058 A | 10/1998 | Ravenscroft et al. |
| RE35,988 E | 12/1998 | Winston et al. |
| 5,843,090 A | 12/1998 | Schuetz |
| 5,851,206 A | 12/1998 | Guglielmi et al. |
| 5,855,578 A | 1/1999 | Guglielmi et al. |
| 5,873,907 A | 2/1999 | Frantzen |
| 5,891,128 A | 4/1999 | Gia et al. |
| 5,919,187 A | 7/1999 | Guglielmi et al. |
| 5,919,204 A | 7/1999 | Lukic et al. |
| 5,919,225 A | 7/1999 | Lau et al. |
| 5,920,975 A | 7/1999 | Morales |
| 5,941,888 A | 8/1999 | Wallace et al. |
| 5,944,726 A | 8/1999 | Blaeser et al. |
| 5,948,017 A * | 9/1999 | Taheri ...................... 623/1.14 |
| 5,957,930 A | 9/1999 | Vrba |
| 5,968,052 A | 10/1999 | Sullivan et al. |
| 5,980,485 A | 11/1999 | Grantz et al. |
| 5,980,514 A | 11/1999 | Kupiecki et al. |
| 5,980,530 A | 11/1999 | Willard et al. |
| 5,984,929 A | 11/1999 | Bashiri et al. |
| 5,989,242 A | 11/1999 | Saadat et al. |
| 5,989,280 A | 11/1999 | Euteneuer et al. |
| 6,004,328 A | 12/1999 | Solar |
| 6,015,429 A | 1/2000 | Lau et al. |
| 6,019,737 A | 2/2000 | Murata |
| 6,019,779 A * | 2/2000 | Thorud et al. ............... 606/198 |
| 6,027,516 A | 2/2000 | Kolobow et al. |
| 6,027,520 A | 2/2000 | Tsugita et al. |
| 6,042,588 A | 3/2000 | Munsinger et al. |
| 6,042,589 A | 3/2000 | Marianne |
| 6,042,605 A | 3/2000 | Martin et al. |
| 6,048,360 A | 4/2000 | Khosravi et al. |
| 6,053,940 A * | 4/2000 | Wijay ....................... 623/1.15 |
| 6,056,759 A | 5/2000 | Fiedler |
| 6,059,779 A | 5/2000 | Mills |
| 6,059,813 A | 5/2000 | Vrba et al. |
| 6,063,101 A | 5/2000 | Jacobsen et al. |
| 6,063,104 A | 5/2000 | Villar et al. |

| | | | |
|---|---|---|---|
| 6,068,634 A | 5/2000 | Lorentzen Cornelius et al. | |
| 6,068,644 A | 5/2000 | Lulo et al. | |
| 6,071,286 A | 6/2000 | Mawad | |
| 6,077,297 A | 6/2000 | Robinson et al. | |
| 6,093,194 A | 7/2000 | Mikus et al. | |
| 6,096,034 A | 8/2000 | Kupiecki et al. | |
| 6,096,045 A | 8/2000 | Del Toro et al. | |
| 6,102,942 A | 8/2000 | Ahari | |
| 6,113,608 A | 9/2000 | Monroe et al. | |
| 6,117,140 A | 9/2000 | Munsinger | |
| 6,120,522 A * | 9/2000 | Vrba et al. | 606/190 |
| 6,123,714 A | 9/2000 | Gia et al. | |
| 6,123,720 A | 9/2000 | Anderson et al. | |
| 6,126,685 A * | 10/2000 | Lenker et al. | 623/1.11 |
| 6,139,524 A | 10/2000 | Killion | |
| 6,139,564 A | 10/2000 | Teoh | |
| 6,156,061 A | 12/2000 | Wallace et al. | |
| 6,156,062 A * | 12/2000 | McGuinness | 623/1.22 |
| 6,161,029 A | 12/2000 | Spreigl et al. | |
| 6,165,178 A | 12/2000 | Bashiri et al. | |
| 6,168,579 B1 | 1/2001 | Tsugita | |
| 6,168,592 B1 | 1/2001 | Kupiecki et al. | |
| 6,168,616 B1 | 1/2001 | Brown, III | |
| 6,168,618 B1 | 1/2001 | Frantzen | |
| 6,174,327 B1 | 1/2001 | Mertens et al. | |
| 6,183,481 B1 | 2/2001 | Lee et al. | |
| 6,183,505 B1 | 2/2001 | Mohn, Jr. et al. | |
| 6,193,708 B1 | 2/2001 | Ken et al. | |
| 6,200,305 B1 | 3/2001 | Berthiaume et al. | |
| 6,203,550 B1 | 3/2001 | Olson | |
| 6,206,888 B1 | 3/2001 | Bicek et al. | |
| 6,214,036 B1 | 4/2001 | Letendre et al. | |
| 6,221,081 B1 | 4/2001 | Mikus et al. | |
| 6,221,097 B1 | 4/2001 | Wang et al. | |
| 6,228,110 B1 | 5/2001 | Munsinger | |
| 6,231,598 B1 | 5/2001 | Berry et al. | |
| 6,238,410 B1 | 5/2001 | Vrba et al. | |
| 6,238,430 B1 * | 5/2001 | Klumb et al. | 623/1.11 |
| 6,241,758 B1 | 6/2001 | Cox | |
| 6,245,097 B1 | 6/2001 | Inoue | |
| 6,248,122 B1 | 6/2001 | Klumb et al. | |
| 6,254,609 B1 | 7/2001 | Vrba et al. | |
| 6,254,611 B1 | 7/2001 | Vrba | |
| 6,254,628 B1 | 7/2001 | Wallace et al. | |
| 6,264,671 B1 | 7/2001 | Stack et al. | |
| 6,264,683 B1 | 7/2001 | Stack et al. | |
| 6,267,783 B1 | 7/2001 | Letendre et al. | |
| 6,270,504 B1 | 8/2001 | Lorentzen Cornelius et al. | |
| 6,273,881 B1 | 8/2001 | Kiemeneij | |
| 6,280,465 B1 | 8/2001 | Cryer | |
| 6,287,331 B1 | 9/2001 | Heath | |
| 6,302,893 B1 | 10/2001 | Limon et al. | |
| 6,306,141 B1 | 10/2001 | Jervis | |
| 6,306,162 B1 | 10/2001 | Patel | |
| 6,319,275 B1 | 11/2001 | Lashinski et al. | |
| 6,342,066 B1 | 1/2002 | Toro et al. | |
| 6,344,041 B1 | 2/2002 | Kupiecki et al. | |
| 6,346,118 B1 | 2/2002 | Baker et al. | |
| 6,350,277 B1 | 2/2002 | Kocur | |
| 6,350,278 B1 | 2/2002 | Lenker et al. | |
| 6,361,637 B2 | 3/2002 | Martin et al. | |
| 6,368,344 B1 | 4/2002 | Fitz | |
| 6,371,962 B1 | 4/2002 | Ellis et al. | |
| 6,375,660 B1 | 4/2002 | Fischell et al. | |
| 6,379,365 B1 | 4/2002 | Diaz | |
| 6,380,457 B1 | 4/2002 | Yurek et al. | |
| 6,383,174 B1 | 5/2002 | Eder | |
| 6,387,118 B1 | 5/2002 | Hanson | |
| 6,391,050 B1 | 5/2002 | Broome | |
| 6,391,051 B2 | 5/2002 | Sullivan, III et al. | |
| 6,395,017 B1 | 5/2002 | Dwyer et al. | |
| 6,409,750 B1 | 6/2002 | Hyodoh et al. | |
| 6,409,752 B1 | 6/2002 | Boatman et al. | |
| 6,413,269 B1 | 7/2002 | Bui et al. | |
| 6,416,536 B1 | 7/2002 | Yee | |
| 6,416,545 B1 | 7/2002 | Mikus et al. | |
| 6,423,090 B1 | 7/2002 | Hancock | |
| 6,425,898 B1 | 7/2002 | Wilson et al. | |
| 6,425,914 B1 | 7/2002 | Wallace et al. | |
| 6,425,915 B1 | 7/2002 | Khosravi et al. | |
| 6,428,489 B1 | 8/2002 | Jacobsen et al. | |
| 6,428,566 B1 | 8/2002 | Holt | |
| 6,432,080 B2 * | 8/2002 | Pederson et al. | 604/103.07 |
| 6,432,129 B2 | 8/2002 | DiCaprio | |
| 6,447,540 B1 | 9/2002 | Fontaine et al. | |
| 6,448,700 B1 | 9/2002 | Gupta et al. | |
| 6,451,025 B1 | 9/2002 | Jervis | |
| 6,451,052 B1 * | 9/2002 | Burmeister et al. | 623/1.16 |
| 6,454,795 B1 * | 9/2002 | Chuter | 623/1.15 |
| 6,458,092 B1 | 10/2002 | Gambale et al. | |
| 6,468,266 B1 | 10/2002 | Bashiri et al. | |
| 6,468,298 B1 | 10/2002 | Pelton | |
| 6,468,301 B1 | 10/2002 | Amplatz et al. | |
| 6,482,227 B1 | 11/2002 | Solovay | |
| 6,485,515 B2 | 11/2002 | Strecker | |
| 6,488,700 B2 * | 12/2002 | Klumb et al. | 623/1.12 |
| 6,517,548 B2 | 2/2003 | Lorentzen Cornelius et al. | |
| 6,517,569 B2 | 2/2003 | Mikus et al. | |
| 6,520,986 B2 | 2/2003 | Martin et al. | |
| 6,530,947 B1 | 3/2003 | Euteneuer et al. | |
| 6,533,805 B1 | 3/2003 | Jervis | |
| 6,533,807 B2 | 3/2003 | Wolinsky et al. | |
| 6,537,295 B2 | 3/2003 | Petersen | |
| 6,558,415 B2 | 5/2003 | Thompson | |
| 6,562,063 B1 | 5/2003 | Euteneuer et al. | |
| 6,562,064 B1 * | 5/2003 | deBeer | 623/1.12 |
| 6,579,297 B2 | 6/2003 | Bicek et al. | |
| 6,579,308 B1 | 6/2003 | Jansen et al. | |
| 6,582,460 B1 | 6/2003 | Cryer | |
| 6,602,226 B1 | 8/2003 | Smith et al. | |
| 6,602,272 B2 | 8/2003 | Boylan et al. | |
| 6,607,539 B1 | 8/2003 | Hayashi et al. | |
| 6,607,551 B1 | 8/2003 | Sullivan et al. | |
| 6,613,079 B1 | 9/2003 | Wolinsky et al. | |
| 6,620,152 B2 | 9/2003 | Guglielmi | |
| 6,623,518 B2 * | 9/2003 | Thompson et al. | 623/1.11 |
| 6,626,938 B1 * | 9/2003 | Butaric et al. | 623/1.28 |
| 6,629,981 B2 | 10/2003 | Bui et al. | |
| 6,645,237 B2 | 11/2003 | Klumb et al. | |
| 6,645,238 B2 | 11/2003 | Smith | |
| 6,656,212 B2 | 12/2003 | Ravenscroft et al. | |
| 6,660,031 B2 | 12/2003 | Tran et al. | |
| 6,660,032 B2 * | 12/2003 | Klumb et al. | 623/1.13 |
| 6,663,660 B2 | 12/2003 | Dusbabek et al. | |
| 6,666,881 B1 | 12/2003 | Richter et al. | |
| 6,669,719 B2 | 12/2003 | Wallace et al. | |
| 6,676,666 B2 | 1/2004 | Vrba et al. | |
| 6,679,910 B1 | 1/2004 | Granada | |
| 6,689,120 B1 | 2/2004 | Gerdts | |
| 6,692,521 B2 | 2/2004 | Pinchasik | |
| 6,699,274 B2 | 3/2004 | Stinson | |
| 6,702,843 B1 | 3/2004 | Brown et al. | |
| 6,709,425 B2 | 3/2004 | Gambale et al. | |
| 6,716,238 B2 | 4/2004 | Elliott | |
| 6,726,714 B2 | 4/2004 | DiCaprio et al. | |
| 6,733,519 B2 | 5/2004 | Lashinski et al. | |
| 6,736,839 B2 | 5/2004 | Cummings | |
| 6,802,858 B2 | 10/2004 | Gambale et al. | |
| 6,814,746 B2 * | 11/2004 | Thompson et al. | 623/1.11 |
| 6,818,014 B2 | 11/2004 | Brown et al. | |
| 6,830,575 B2 | 12/2004 | Stenzel et al. | |
| 6,833,002 B2 | 12/2004 | Stack et al. | |
| 6,833,003 B2 | 12/2004 | Jones et al. | |
| 6,843,802 B1 | 1/2005 | Villalobos et al. | |
| 6,858,034 B1 | 2/2005 | Hijlkema et al. | |
| 6,860,899 B1 * | 3/2005 | Rivelli, Jr. | 623/1.22 |

| | | |
|---|---|---|
| 6,875,212 B2 | 4/2005 | Shaolian et al. |
| 6,936,058 B2 * | 8/2005 | Forde et al. .................. 606/200 |
| 6,936,065 B2 | 8/2005 | Khan et al. |
| 6,989,024 B2 | 1/2006 | Hebert et al. |
| 7,011,673 B2 | 3/2006 | Fischell et al. |
| 7,172,620 B2 | 2/2007 | Gilson |
| 7,300,460 B2 | 11/2007 | Levine et al. |
| 7,393,357 B2 | 7/2008 | Stelter et al. |
| 2001/0020173 A1 * | 9/2001 | Klumb et al. ................ 606/194 |
| 2001/0034548 A1 | 10/2001 | Vrba et al. |
| 2001/0047185 A1 * | 11/2001 | Satz ........................... 606/198 |
| 2001/0049547 A1 | 12/2001 | Moore |
| 2001/0049550 A1 | 12/2001 | Martin et al. |
| 2002/0002397 A1 | 1/2002 | Martin et al. |
| 2002/0032431 A1 | 3/2002 | Kiemeneij |
| 2002/0035393 A1 | 3/2002 | Lashinski et al. |
| 2002/0040236 A1 | 4/2002 | Lau et al. |
| 2002/0045928 A1 | 4/2002 | Boekstegers |
| 2002/0045930 A1 | 4/2002 | Burg et al. |
| 2002/0049490 A1 | 4/2002 | Pollock et al. |
| 2002/0068966 A1 | 6/2002 | Holman et al. |
| 2002/0072729 A1 | 6/2002 | Hoste et al. |
| 2002/0077693 A1 * | 6/2002 | Barclay et al. ............. 623/1.13 |
| 2002/0095147 A1 | 7/2002 | Shadduck |
| 2002/0095168 A1 | 7/2002 | Griego et al. |
| 2002/0099433 A1 | 7/2002 | Fischell et al. |
| 2002/0120322 A1 | 8/2002 | Thompson et al. |
| 2002/0120323 A1 * | 8/2002 | Thompson et al. ......... 623/1.11 |
| 2002/0120324 A1 | 8/2002 | Holman et al. |
| 2002/0138129 A1 | 9/2002 | Armstrong et al. |
| 2002/0147491 A1 | 10/2002 | Khan et al. |
| 2002/0151967 A1 * | 10/2002 | Mikus et al. ................ 623/1.22 |
| 2002/0161342 A1 | 10/2002 | Rivelli et al. |
| 2002/0169494 A1 | 11/2002 | Mertens et al. |
| 2002/0188341 A1 | 12/2002 | Elliott |
| 2002/0188344 A1 * | 12/2002 | Bolea et al. ................ 623/1.11 |
| 2003/0014103 A1 | 1/2003 | Inoue |
| 2003/0018319 A1 | 1/2003 | Kiemeneij |
| 2003/0036768 A1 | 2/2003 | Hutchins et al. |
| 2003/0040771 A1 | 2/2003 | Hyodoh et al. |
| 2003/0040772 A1 | 2/2003 | Hyodoh et al. |
| 2003/0055377 A1 | 3/2003 | Sirhan et al. |
| 2003/0065375 A1 | 4/2003 | Eskuri |
| 2003/0069521 A1 | 4/2003 | Reynolds et al. |
| 2003/0105508 A1 | 6/2003 | Johnson et al. |
| 2003/0135266 A1 | 7/2003 | Chew et al. |
| 2003/0149467 A1 | 8/2003 | Linder et al. |
| 2003/0163156 A1 | 8/2003 | Hebert et al. |
| 2003/0163189 A1 | 8/2003 | Thompson et al. |
| 2004/0010265 A1 | 1/2004 | Karpiel |
| 2004/0049547 A1 | 3/2004 | Matthews et al. |
| 2004/0093063 A1 | 5/2004 | Wright et al. |
| 2004/0097917 A1 | 5/2004 | Keane |
| 2004/0127912 A1 | 7/2004 | Rabkin et al. |
| 2004/0193178 A1 | 9/2004 | Nikolchev |
| 2004/0193179 A1 | 9/2004 | Nikolchev |
| 2004/0193246 A1 | 9/2004 | Ferrera |
| 2004/0220585 A1 | 11/2004 | Nikolchev |
| 2004/0260377 A1 | 12/2004 | Flomenblit et al. |
| 2005/0049668 A1 | 3/2005 | Jones et al. |
| 2005/0049669 A1 | 3/2005 | Jones et al. |
| 2005/0049670 A1 | 3/2005 | Jones et al. |
| 2005/0080430 A1 | 4/2005 | Wright, Jr. et al. |
| 2005/0096724 A1 | 5/2005 | Stenzel et al. |
| 2005/0209670 A1 | 9/2005 | George et al. |
| 2005/0209671 A1 | 9/2005 | Ton et al. |
| 2005/0209672 A1 | 9/2005 | George et al. |
| 2005/0209675 A1 | 9/2005 | Ton et al. |
| 2005/0220836 A1 | 10/2005 | Falotico et al. |
| 2005/0246010 A1 | 11/2005 | Alexander et al. |
| 2006/0085057 A1 | 4/2006 | George et al. |
| 2006/0136037 A1 | 6/2006 | DeBeer et al. |
| 2006/0247661 A1 | 11/2006 | Richards et al. |
| 2006/0270948 A1 | 11/2006 | Viswanathan et al. |
| 2006/0271097 A1 | 11/2006 | Ramzipoor et al. |
| 2006/0276886 A1 | 12/2006 | George et al. |
| 2007/0027522 A1 | 2/2007 | Chang et al. |
| 2007/0043419 A1 | 2/2007 | Nikolchev et al. |
| 2007/0073379 A1 | 3/2007 | Chang et al. |
| 2007/0100414 A1 | 5/2007 | Licata et al. |
| 2007/0100415 A1 | 5/2007 | Licata |
| 2007/0100416 A1 | 5/2007 | Licata |
| 2007/0100417 A1 | 5/2007 | Licata |
| 2007/0100418 A1 | 5/2007 | Licata |
| 2008/0015541 A1 | 1/2008 | Rosenbluth et al. |
| 2008/0071309 A1 | 3/2008 | Mazzocchi et al. |
| 2008/0221666 A1 | 9/2008 | Licata et al. |

FOREIGN PATENT DOCUMENTS

| | | |
|---|---|---|
| EP | 0667 132 | 8/1995 |
| EP | 0 747 021 | 12/1996 |
| EP | 1 157 673 | 11/2001 |
| EP | 1518515 | 3/2005 |
| JP | 2002-538938 | 11/2002 |
| WO | WO 97/12563 | 4/1997 |
| WO | WO 97/48343 A1 | 12/1997 |
| WO | WO 98/23241 | 6/1998 |
| WO | WO 99/04728 | 2/1999 |
| WO | WO 99/08740 | 2/1999 |
| WO | WO 00/18330 | 4/2000 |
| WO | WO 00/56248 | 9/2000 |
| WO | WO 01/78627 | 10/2001 |
| WO | WO 03/073963 | 9/2003 |
| WO | WO 2004/087006 A2 | 10/2004 |
| WO | WO 2005/092241 | 10/2005 |
| WO | WO 2005/094727 | 10/2005 |

OTHER PUBLICATIONS

Bonsignore, Craig, "A Decade of Evolution in Stent Design" Cordis Corporation Nitinol Devices & Components. 47533 Westinqhouse Drive, Fremont. California 94539.
Fischell, M.D. FACC, Tim A.. "A Fixed Guidewire Stent Delivery System Rationale and Design" TCT. Washington. D.C. (Sep. 24, 2002).
Poncept, Philippe P., "Nitinol Medical Device Design Considerations" MEMRY Corporation. 4065 Campbell Avenue, Menlo Park. California 94025. pp. 1-12.
Definitions of "abut" and "wire"—Random House College Dictionary, 1980, New York, 7 and 510.
Duerig et al., "An overview of superelastic stent design" Min fnvas Ther & Affied Technol. 9(3/4 ):235-246 (2000).
Schuessler et al., Stent Materials and Manufacturing: Requirements and Possibilities/Opportunities, ASM Materials & Processes for Medical Devices, Anaheim, CA. (Sep. 8-10, 2003).
Stoeckel et al., "A Survey of Stent Designs" Min Invas Ther & Allied Technol 11(4):137-147 (2002).
Welt et al. "Coronary Artery Stents: Design and Biologic Considerations" Cardiology Special Edition 9(2) 9-14(2003).
Rogers, C. "DES Overview: Agents: release mechanism and stent platform", PowerPoint Presentation, 51 pages total.
International Search Report and Written Opinion of PCT Application No. PCT/US2006/034311, mailed Mar. 22, 2007, 7 pages total.
International Search Report and Written Opinion of PCT Application No. PCT/US2006/34130, mailed Nov. 23, 2007, 8 pages total.
International Search Report and Written Opinion of PCT Application No. PCT/US2004/008909, mailed Sep. 24, 2004, 6 pages total.
International Preliminary Report on Patentability of PCT Application No. PCT/US2006/34130, dated Oct. 14, 2008, 8 pages total.
Supplementary European Search Report of EP Application No. 06802753.1, mailed Dec. 4, 2008, 9 pages total.
Communication from the Examining Division of EP Application No. 06802753.1, mailed Mar. 18, 2009, 1 page total.

* cited by examiner

TWIST-DOWN IMPLANT DELIVERY TECHNOLOGIES

CROSS REFERENCE

This filing is a continuation-in-part of U.S. patent application "Implant Delivery Technologies" (Ser. No. 10/550,707) filed Sep. 26, 2005, which is a continuation of PCT Patent Application, "Implant Delivery Technologies" (U.S. 2004/008909) filed Mar. 23, 2004, which claims the benefit of U.S. Provisional Patent Applications "Implant Delivery Device" (Ser. No. 60/458,323), filed Mar. 26, 2003 and "Implant Delivery Device II" (Ser. No. 60/462,219), filed Apr. 10, 2003 as well as U.S. patent applications "Implant Delivery Technologies" (Ser. No. 10/745,778), "Multiple Joint Implant Delviery Systems for Sequentially-Controlled Implant Deployment" (Ser. No. 10/746,452), and "Balloon Catheter Lumen Based Stent Delivery Systems" (Ser. No. 10/746,455), each filed Dec. 24, 2003, and "Sliding Restraint Stent Delivery Systems" (Ser. No. 10/792,684), filed Mar. 2, 2004 now abandoned. Each of the above-referenced applications is incorporated by reference herein in its entirety.

BACKGROUND

Implants such as stents and occlusive coils have been used in patients for a wide variety of reasons. One of the most common "stenting" procedures is carried out in connection with the treatment of atherosclerosis, a disease which results in a narrowing and stenosis of body lumens, such as the coronary arteries. At the site of the narrowing (i.e., the site of a lesion) a balloon is typically dilatated in an angioplasty procedure to open the vessel. A stent is set in apposition to the interior surface of the lumen in order to help maintain an open passageway. This result may be affected by means of scaffolding support alone or by virtue of the presence of one or more drugs carried by the prosthesis to aid in the prevention of restenosis.

Various stent designs exist and are in use today, but self-expandable and balloon-expandable stent systems and their related deployment techniques are now predominant. Examples of currently available self-expandable stents are the Magic WALLSTENT® stents and Radius stents (Boston Scientific). The Cypher® stent (Cordis Corporation) is a commonly used balloon-expandable stent. Additional self-expanding stent background is presented in: "An Overview of Superelastic Stent Design," Min. Invas Ther & Allied Technol 822: 9(3/4) 235-246, "A Survey of Stent Designs," Min. Invas Ther & Allied Technol 822: 11(4) 137-147, and "Coronary Artery Stents: Design and Biologic Considerations," Cardiology Special Edition, 823: 9(2) 9-14, "Clinical and Angiographic Efficacy of a Self-Expanding Stent" Am Heart J 823: 145(5) 868-874.

Because self-expanding prosthetic devices need not be set over a balloon (as with balloon-expandable designs), self-expanding stent delivery systems can be designed to a relatively smaller outer diameter than their balloon-expandable counterparts. As such, self-expanding stents may be better suited to reach the smallest vasculature or achieve access in more difficult cases. To realize such benefits, however, there continues to be a need in developing improved stents and stent delivery systems.

The present invention offers a stent and system having a space-efficient mode of stent delivery.

SUMMARY

Variations of the invention hold a radially-expandable prosthesis (such as a stent) in a compressed configuration for delivery either with or without the use of a tubular restraint covering at least a portion of the prosthesis body. By employing a twist-down mode for collapsing the diameter of the stent, the system does not require a sleeve to retain the stent or, if a sleeve is provided, the stent does not strain against it as would otherwise be the case. As discussed herein, stents used in the inventive systems have projections that include interface features for mating or seating with complimentary features on the delivery device that allow for the stent to be delivered in a collapsed (twisted-down) state and, when desired, expanded for implantation.

Delivery systems according to the present invention may include use-manipulable element(s) that allow for actuation of the subject system. These elements may include handles, finger actuators, or other means as commonly known and used for such devices. They may allow for rotation, axial movement, withdrawal of a sheath, or other manipulations required to deploy or load a prosthesis as discussed herein.

Stents employed in the systems are tubular-type members (i.e., they are not coil stents). The stents are lattice, cage or successive linked ring type structures or they are mesh-like woven or assembled bodies. Most often, the stents are produced by cutting round tubing. However, other means or modes of manufacture are possible as well.

In one variation of the delivery system, a body or shaft of a delivery guide is provided in the form of a tube or sleeve that includes projections in the form of hooks at a distal end (where the hook portion extends out-of-plane). The body is advantageously made of hypotubing in order to manufacture hooks integral thereto. Complementary hooks may be formed distal thereto and supported by a core member over which the sleeve rides. The distal hooks may be formed in connection with a ring or be provided otherwise.

Similar construction may be employed in another variation of the invention, in which the hooks or hook-type projection features are oriented substantially circumferentially. In this fashion, interlocking ends of the stent and hooks lie next to one another or occupy the same circumferential region. In any case, the hooks (typically numbering at least two per side of the implant to balance forces) are dimensioned with a prong and recess suited for receipt of a stent. The hooks may be J-shaped, T-shaped or otherwise configured as elaborated upon below.

In yet another variation of the invention, one or more ends of the stent and interfacing delivery system may include axially-directed interface features. Rather than utilizing an interlocking interface, the projections employed in these variations of the invention provide lateral capture and axial disengagement without a requirement for out-of-plane movement.

Irregardless of the manner in which the respective interface or mating portions are configured, a twisting mode of stent compression and retention is employed. Stent release is accomplished by releasing the twist or torque (possibly tension as well) that holds a given stent in a collapsed profile or by other means including radial release and foreshortening of the stent to pull out of the interface member to allow it to then unwind from the twisted, collapsed profile.

The combination of interfacing stent and delivery system features may work alone, or in conjunction with supplemental hold-down features. Sleeve and band type members are discussed herein, though other options are possible as well. For example, generic concepts expressed herein may be supported and/or practiced employing variations of the invention as set forth in U.S. patent application Ser. No. 11/265,999, entitled "Indirect-Release Implant Delivery Systems," filed on even date herewith and incorporated by reference in its entirety for this or any other purpose.

Methodology described in association with the devices disclosed and implicit to their use also forms part of the invention. Such methodology may include that associated with completing an angioplasty, bridging an aneurysm, deploying radially-expandable anchors for pacing leads or an embolic filter, or placement of a prosthesis within neurovasculature, an organ selected from the kidney and liver, within reproductive anatomy such as selected vasdeferens and fallopian tubes or other applications.

DEFINITIONS

The term "stent" as used herein includes any stent, such as coronary artery stents, other vascular prosthesis, or other radially expanding or expandable prosthesis or scaffold-type implant suitable for the noted treatments or otherwise. Exemplary structures include wire mesh or lattice patterns and coils, though others may be employed in the present invention.

A "self-expanding" stent as used herein is a scaffold-type structure (serving any of a number of purposes) that expands from a reduced-diameter (be it circular or otherwise) configuration to an increased-diameter configuration. The mechanism for shape recover may be elastic or pseudoelastic. While it is generally desireable to employ an alloy (such as nickel-titanium, or Nitinol alloy) set for use as a superelastic alloy, it may alternatively employ thermal shape memory properties to drive expansion upon release.

A "wire" as used herein generally comprises a common metallic member. However, the wire may be coated or covered by a polymeric material (e.g., with a lubricious material such as TEFLON®, i.e., PolyTetraFluoroEthelyne or PTFE) or otherwise. Still further, the "wire" may be a hybrid structure with metal and a polymeric material (e.g., Vectran™, Spectra™, Nylon, etc.) or composite material (e.g., carbon fiber in a polymer matrix). The wire may be a filament, bundle of filaments, cable, ribbon or in some other form. It is generally not hollow.

A "corewire" or "core member" may be use interchangeably and, as referred to herein, has a wire form and may be made from any biocompatible material including; but not limited to, stainless steel and any of its alloys; titanium alloys, e.g., Ni—Ti alloys; other shape memory alloys (i.e., SMAs); tantalum; polymers, e.g., polyethylene and copolymers thereof, polyethylene terephthalate or copolymers thereof, nylon, silicone, polyurethane fluoropolymers, poly (vinyl-chloride), and combinations thereof.

An "inner member" as disclosed herein includes a core member or a corewire and a cladding, cladding sections or a cladding layer which covers or surrounds at least a portion of the core member or corewire. The two may be bonded together or otherwise connected/interconnected.

A "cladding" as referred to herein means an outer layer of material which is bonded to a core member or a core wire. As with the "wire" discussed above, the material defining the cladding may be metallic, polymeric or a hybrid of thereof or a composite material. The cladding material may have the same flexibility or greater flexibility than the member to which it is bonded to so as not impeded the member's flexibility.

A "hypotube" or "hypotubing" as referred to herein means small diameter tubing in the size range discussed below, generally with a thin wall. The hypotube may specifically be hypodermic needle tubing. Alternatively, it maybe wound or braided cable tubing, such as provided by Asahi Intec Co., Ltd. or otherwise. As with the "wire" discussed above, the material defining the hypotube may be metallic, polymeric or a hybrid of metallic and polymeric or composite material.

A "sleeve" as referred to herein may be made of hypotubing or otherwise constructed. The sleeve may be a tubular member, or it may have longitudinal opening(s). It is an outer member, able to slidingly. receive and hold at least a portion of an inner member.

An "atraumatic tip" may comprise a plurality of spring coils attached to a tapered wire section. At a distal end of the coils typically terminate with a bulb or ball that is often made of solder. In such a construction, the coils and/or solder are often platinum alloy or another radiopaque material. The coils may also be platinum, or be of another material. In the present invention, the wire section to which the coils are attached may be tapered, but need not be tapered. In addition, alternate structures are possible. In one example, the atraumatic tip may comprise a molded tantalum-loaded 35 durometer Pebax™ tip. However constructed, the atraumatic tip may be straight or curved, the latter configuration possibly assisting in directing or steering the delivery guide to a desired intravascular location.

To "connect" or to have or make a "connection" between parts refers to fusing, bonding, welding (by resistance, laser, chemically, ultrasonically, etc.), gluing, pinning, crimping, clamping or otherwise mechanically or physically joining, attaching or holding components together (permanently or temporarily).

To "bond" or form a "bonding" between structures refers to forming an intimate contact between the structures, typically where the contanct is intended to be permanent. The bond or bonding may be achieved by any known means and process including, but not limited to, pressure rolling, extruding, drawing, swaging and adhesion.

"Radiopaque markers" are understood to be markers or features of the various delivery system components, corewire or implant that may be employed to facilitate visualization of the system components. As such, various platinum (or other radiopaque material) bands or other markers (such as tantalum plugs) may be variously incorporated into the system. Alternatively, or additionally, the stent may be made of radiopaque material or incorporate them. Especially where the stent employed may shorten somewhat upon deployment, it may also be desired to align radiopaque features with the expected location (relative to the body of the inner member) of the stent upon deployment. A filter used with the subject devices may also be made of radiopaque material for the same reasons.

"Releaseably locked" or "lockable" is understood to mean that the lockable components may be prevented from accidentally moving. For example, a handle may be releasably locked to a delivery guide by use of some mechanical stop or fitting (e.g., such as a collet that must be loosened, a latch that must be disengaged, a key that must be removed, etc.). Many common examples of mechanical stops or fittings are found in medical devices where pre-mature actuation of one or more components has the potential to cause trauma to a patient.

BRIEF DESCRIPTION OF THE DRAWINGS

The Figures shown herein are not necessarily drawn to scale, with some components and features being exaggerated for clarity. Each of the Figures diagrammatically illustrates aspects of the invention. Of these.

DETAILED DESCRIPTION

Various exemplary embodiments of the invention are described below. Reference is made to these examples in a non-limiting sense. They are provided to illustrate more broadly applicable aspects of the present invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. All such modifications are intended to be within the scope of the claims made herein.

Figure 1:
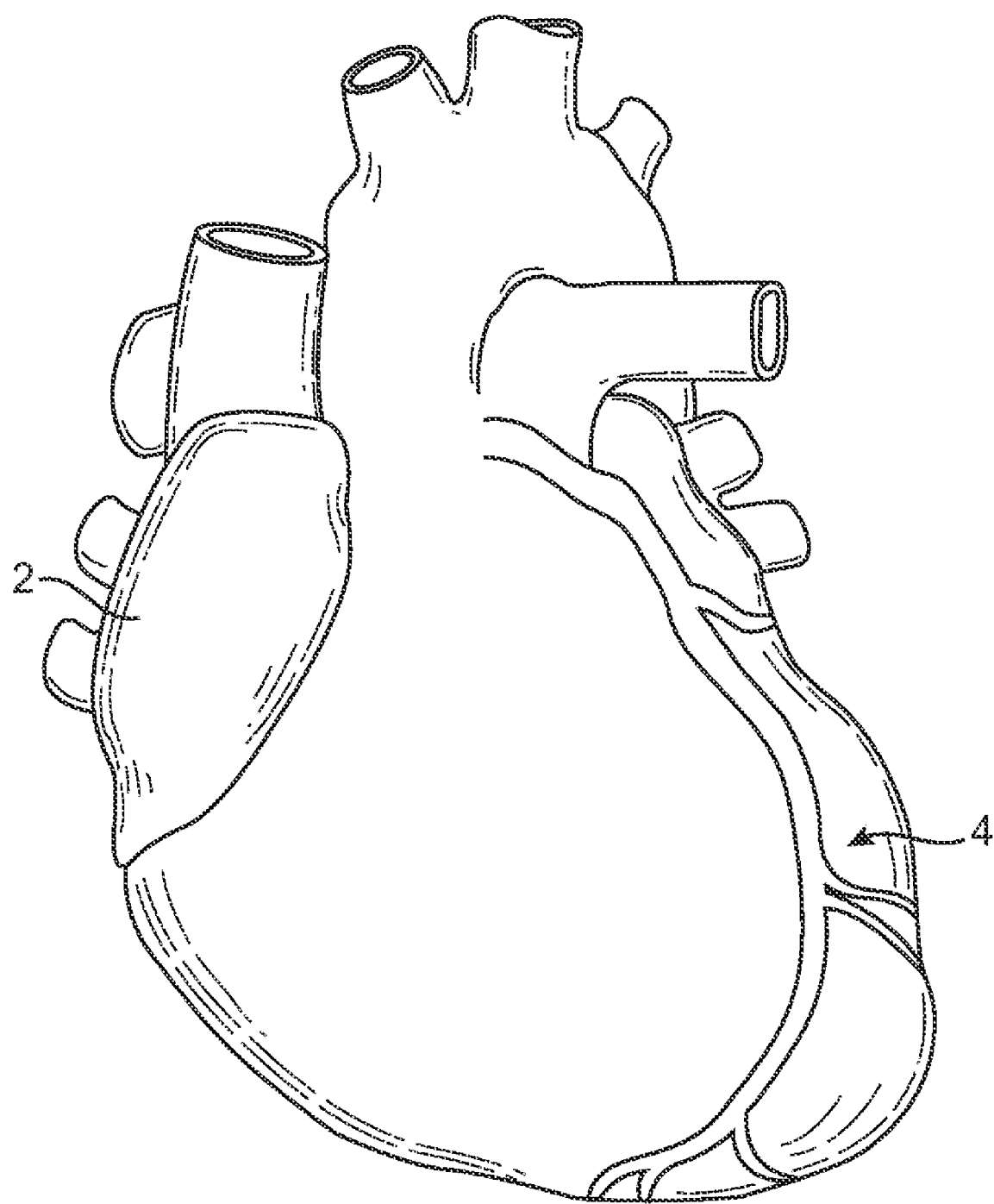
FIG. 1 shows a heart in which its vessels may be the subject of one or more angioplasty and stenting procedures.

In light of this framework, FIG. 1 shows a heart 2 in which its vessels may be the subject of one or more angioplasty and/or stenting procedures. To date, however, significant difficulty or impossibility is confronted in reaching smaller coronary arteries 4. If a stent and a delivery system could be provided for accessing such small vessels and other difficult anatomy, an additional 20 to 25% coronary percutaneous procedures could be performed with such a system. Such potential offers opportunity for huge gains in human healthcare and a concomitant market opportunity—with the further benefit of avoiding loss of income and productivity of those treated.

Features of the present invention are uniquely suited for a system able to reach small vessels (though use of the subject systems s not limited to such a setting.) By "small" coronary vessels, it is meant vessels having an inside diameter from between about 1.5 to 2 mm and up to about 3 mm in diameter. These vessels include, but are not limited to, the Posterior Descending Artery (PDA), Obtuse Marginal (OM) and small diagonals. Conditions such as diffuse stenosis and diabetes produce situations that represent other access and delivery challenges that can be addressed with a delivery system according to the present invention. Other extended treatment areas addressable with the subject systems include vessel bifurcations, chronic total occlusions (CTOs), and prevention procedures (such as in stenting of vulnerable plaque).

It may be preferred to use a drug eluting stent (DES) in such an application to aid in preventing restenosis. A review of suitable drug coatings and available vendors is presented in "DES Overview: Agents, release mechanism, and stent platform" a presentation by Campbell Rogers, MD incorporated by reference in its entirety. However, bare-metal stents may be employed in the present invention.

Examples of various therapeutic agents that may be used in or on the subject prosthesis include, but are not limited to, antibiotics, anticoagulants, antifungal agents, anti-inflammatory agents, antineoplastic agents, antithrombotic agents, endothelialization promoting agents, free radical scavengers, immunosuppressive agents, antiproliferative agents, thrombolytic agents, and any combination thereof. The therapeutic agent may be coated onto the implant, mixed with a biodegradable polymer or other suitable temporary carrier and then coated onto the implant, or, when the implant is made from a polymeric material dispersed throughout the polymer. The agent can be directly applied to the stent surface(s), or introduced into pockets or an appropriate matrix set over at least an outer portion of the stent.

While some might argue that the particular role and optimal usage of self expanding stents has yet to be defined, they offer an inherent advantage over balloon expandable stents. The latter type of devices produce "skid mark" trauma (at least when delivered uncovered upon a balloon) and are associated with a higher risk of end dissection or barotraumas caused at least in part by high balloon pressures and related forces when deforming a balloon-expandable stent for deployment.

Yet, with an appropriate deployment system, self-expanding stents may offer one or more of the following advantages over balloon-expandable models: 1) greater accessibility to distal, tortuous and small vessel anatomy—by virtue of decreasing crossing diameter and increasing compliance relative to a system requiring a deployment balloon, 2) sequentially controlled or "gentle" device deployment, 3) use with low pressure balloon pre-dilatation (if desirable) to reduce barotraumas, 4) strut thickness reduction in some cases reducing the amount of "foreign body" material in a vessel or other body conduit, 5) opportunity to treat neurovasculature—due to smaller crossing diameters and/or gentle delivery options, 6) the ability to easily scale-up a successful treatment system to treat larger vessels or vice versa, 7) a decrease in system complexity, offering potential advantages both in terms of reliability and system cost, 8) reducing intimal hyperplasia, and 9) conforming to tapering anatomy— without imparting complimentary geometry to the stent (though this option exists as well).

Figure 2A:
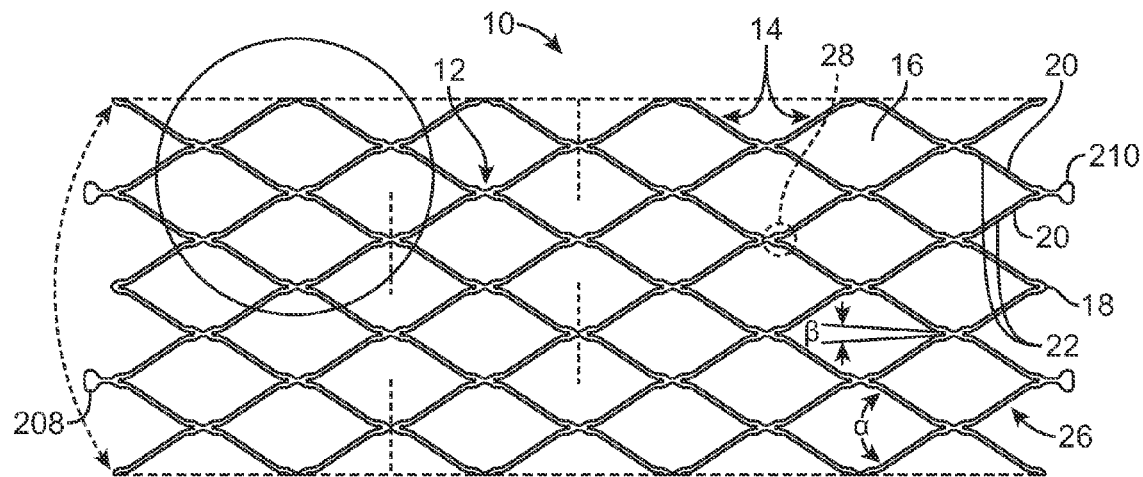
FIG. 2A shows an expanded stent cut pattern as may be used in producing a stent according to a first aspect of the invention.

At least some of these noted advantages may be realized using a stent 10 as shown in FIG. 2A. The stent pattern pictured is well suited for use in small vessels. It may be collapsed to an outer diameter of about 0.018 inch (0.46 mm), or even smaller to about 0.014 inch (0.36 mm)—including the restraint/joint used to hold it down—and expanded to a size (fully unrestrained) between about 1.5 mm (0.059 inch) or 2 mm (0.079 inch) or 3 mm (0.12 inch) and about 3.5 mm (0.14 inch).

In use, the stent will be sized so that it is not fully expanded when fully deployed against the wall of a vessel in order to provide a measure of radial force thereto (i.e., the stent will be "oversized" as discussed above). The force will secure the stent and offer potential benefits in reducing intimal hyperplasia and vessel collapse or even pinning dissected tissue in apposition.

Stent 10 preferably comprises NiTi that is superelastic at or below room temperature (i.e., as in having an Af as low as 15 degrees C. or even 0 degrees C.). Also, the stent is preferably electropolished to improve biocompatibility and corrosion and fatigue resistance. The stent may be a DES unit as referenced above. The stent may be coated with gold and/or platinum to provide improved radiopacity for viewing under medical imaging.

For a stent able to collapse to an outer diameter of about 0.012 inches and expand to about 3.5 mm, the thickness of the NiTi is about 0.0025 inch (0.64 mm). Such a stent is designed for use in a 3 mm vessel or other body conduit, thereby providing the desired radial force in the manner noted above. Further information regarding radial force parameters in coronary stents may be noted in the article, "Radial Force of Coronary Stents: A Comparative Analysis," Catheterization and Cardiovascular Interventions 46: 380-391 (1999), incorporated by reference herein in its entirety.

In one manner of production, the stent in FIG. 2A is laser or EDM cut from round NiTi tubing, with the flattened-out pattern shown wrapping around the tube as indicated by dashed lines. In such a procedure, the stent is preferably cut in its fully-expanded shape. By initially producing the stent to full size, the approach allows cutting finer details in comparison to simply cuffing a smaller tube with slits and then heat-expanding/annealing it into its final (working) diameter. Avoiding post-cutting heat forming also reduces production cost as well as the above-reference effects.

Figure 2B:
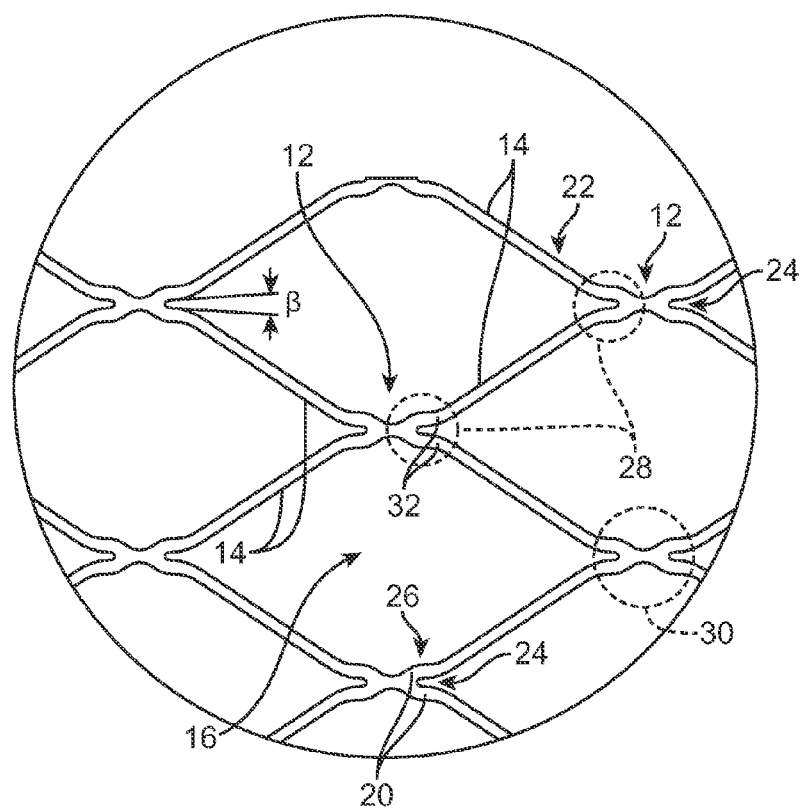
FIG. 2B shows a stent cut pattern for a second stent produced according to another aspect of the present invention.

Regarding the finer details of the subject stent, as readily observed in the detail view provided in FIG. 2B, necked down bridge sections 12 are provided between axially/horizontally adjacent struts or arms/legs 14, wherein the struts define a lattice of closed cells 16. Such a closed cell design facilitate twist-down because the otherwise free ends of an open ended cell (or successive ring) design have a tendency to lift-off in a radial direction due to complex stress distributions.

In certain variations of the invention, however, the bridge sections can be strategically separated or opened as indicated by the broken lines in FIG. 2A. Doing so disrupts the closed cell pattern discussed above, but may increase stent conformability to tortuous anatomy. One situation in which such modification may be useful is in those variations of the invention employing a sleeve or sheath overlying the stent. In any case, to facilitate such tuning of the stent, the bridge sections are preferably sufficiently long so that fully rounded ends may be formed internally to the lattice just as shown at terminal ends 18 of the cells not carrying stent/delivery system interface features.

As for the optional double-concave profile of each strut bridge 12 shown, this form is advantageous in that it reduces material width (relative to what would otherwise be presented by a parallel side profile) to improve flexibility and thus trackability and conformability of the stent within the subject anatomy while still maintaining the option for separating/breaking the cells apart. Whether cut to provide rounded end portions or adjoined by a bridge section 12, strut junction sections 28 connect circumferentially or vertically adjacent struts (as illustrated). Where no bridge sections are provided, the junction sections can be unified between horizontally adjacent stent struts as indicated in region 30.

Further optional features of stent 10 are employed in the strut junction sections 28 of the design. Specifically, strut ends 20 increase in width relative to medial strut portions 22. Such a configuration distributes bending (during collapse of the stent) preferentially toward the mid region of the struts. For a given stent diameter and deflection, longer struts allow for lower stresses within the stent (and, hence, a possibility of higher compression ratios). Shorter struts allow for greater radial force (and concomitant resistance to a radially applied load) upon deployment.

In order to increase stent compliance so that it collapses as much as possible, accommodation is made for the stiffer strut ends 20 provided in the design shown in FIG. 2A. Namely, the gap 24 between the strut ends 22 is set at a smaller angle as if the stent were already partially collapsed in that area. Thus, the smaller amount of angular deflection that occurs at ends 20 can bring the sections parallel (or nearly so) when the strut medial portions 22 are so-arranged. In the variation of the invention in FIG. 2A, radiused or curved sections 26 provide a transition from a medial strut angle $\alpha$ (ranging from about 85 degrees to about 60 degrees) to an end strut angle $\beta$ (ranging from about 30 to about 0 degrees) at the strut junctions 28 and/or extensions therefrom.

In addition, it is noted that gap 24 an angle $\beta$ may actually be configured to completely close prior to fully collapsing angle $\alpha$. The stent shown is not so-configured. Still, the value of doing so would be to limit the strains (and hence, stresses) at the strut ends 22 and cell end regions 18 by providing a physical stop to prevent further strain.

In the detail view of FIG. 2B, angle $\beta$ is set at 0 degrees. The gap 24 defined thereby by virtue of the noticeably thicker end sections 20 at the junction result in very little flexure along those lever arms. The strut medial portions are especially intended to accommodate bending. In addition, a hinging effect at the corner or turn 32 of junction section 28 may allow the strut to swing around angle $\alpha$ to provide the primary mode for compression of the stent.

Additional features of interest in the stent design include near and far delivery system interface mating portions 208 and 210, respectively. These elements are formed within-projections 212 that may be integral to the prosthesis 82 (e.g., when the prosthesis is constructed from a single tube of material, or when a number of wire-type elements are woven to form the body where the ends of the elements form the prosthesis). Alternatively, the projections may be affixed or connected to the stent (e.g., via welding, adhesive bonding, fastening, etc.). In another variation of the invention, the projections may comprise polymeric material that is coated onto the prosthesis 82. Other modes of construction are possible as well. Further details of the projections and respective mating portions are discussed in detail below. Suffice it to say here that elements are sufficiently "floppy" and/or rounded to offer an atraumatic interface with opposing tissue.

Figure 3A:
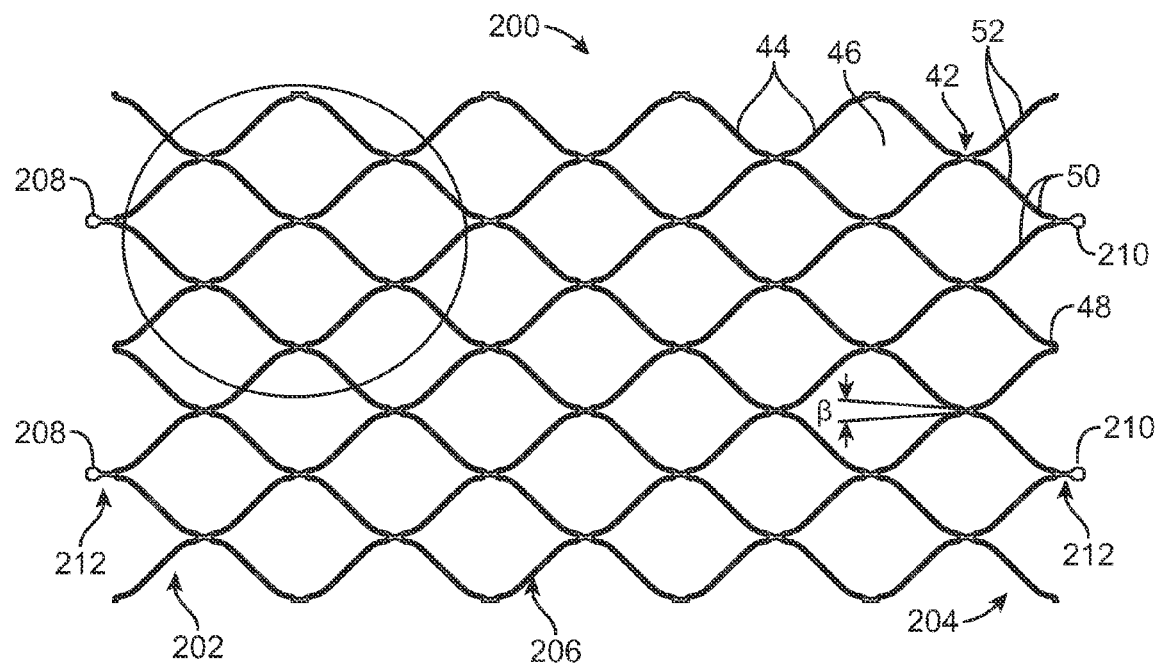
FIG. 3A shows an expanded stent cut pattern as may be used in producing a stent according to a first aspect of the invention.
Figure 3B:
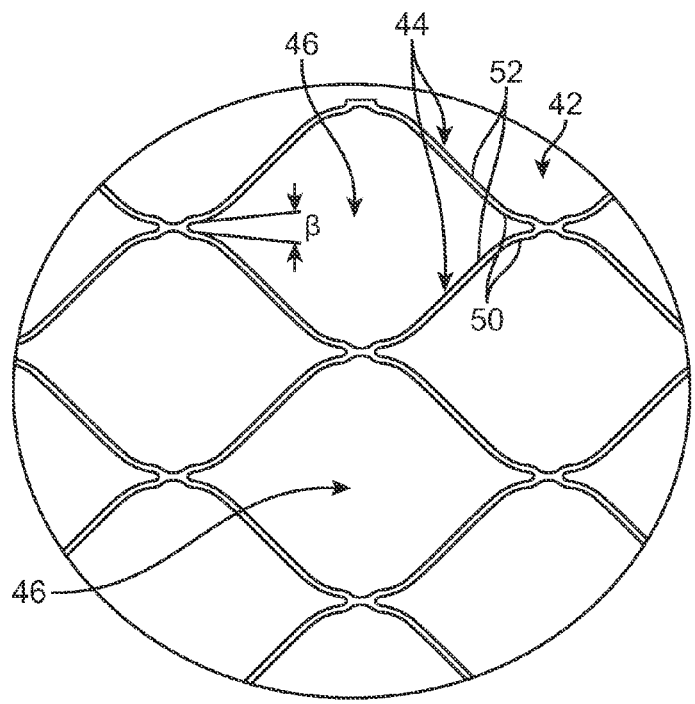
FIG. 3B shows a stent cut pattern for a second stent produced according to another aspect of the present invention.

The stent pattern shown in FIG. 3A and detailed in FIG. 3B offers certain similarities as well as some major differences from the stent pattern presented in FIGS. 2A and 2B. As in the variation above, stent 82 includes necked down bridge sections 42 provided between adjacent struts or arms/legs 44, wherein the struts define a lattice of closed cells 46. In addition, terminal ends 48 of the cells are preferably rounded-off so as to be atraumatic, as may mating portions 208, 210.

Furthermore, the bridge sections 42 of stent 82 can be separated for compliance purposes. In addition, they may be otherwise modified (e.g., as described above) or even eliminated. Also, in each design, the overall dimensions of the cells and indeed the number of cells provided to define axial length and/or diameter may be varied (as indicated by the vertical and horizontal section lines in FIG. 3A).

Like the previous stent design, strut ends 50 may offer some increase in width relative to medial strut portions 52. However, as shown in FIG. 3B, as compared to FIG. 2B, the angle β is relatively larger. Such a configuration is not concerned with developing a hinge section and a relatively stiffer outer strut section. Instead, angle β in the FIG. 3A/3B design is meant to collapse and the strut ends are meant to bend in concert with the medial strut portions so as to essentially straighten-out upon collapsing the stent, generally forming tear-drop spaces between adjacent struts. This approach offers a stress-reducing radius of curvature where struts join, and maximum stent compression.

The "S" curves defined by the struts are produced in a stent cut to a final or near final size (as shown in FIGS. 3A and 3B). The curves are preferably determined by virtue of their origination in a physical or computer model that is expanded from a desired compressed shape to the final expanded shape. So derived, the stent can be compressed or collapsed under force to provide an outer surface profile that is as solid or smooth and/or cylindrical as possible or feasible. Such action is enabled by distribution of the stresses associated with compression to generate stains to produce the intended compressed and expanded shapes. This effect is accomplished in a design unaffected by one or more expansion and heat setting cycles that otherwise deteriorate the quality of the superelastic NiTi stent material. Further details regarding the "S" stent design and alternative stent constructions as may be used in the present invention are disclosed in U.S. Provisional Patent Application Ser. No. 60/619,437, entitled, "Small Vessel Stent Designs", filed October 14, 824 and incorporated herein by reference in its entirety.

For use in the present invention, it has been discovered that the design in FIGS. 3A and 3B not only compresses to a closely cylindrical profile, but that it maintains such a shape when twisted. Not to be bound by a particular theory, but it is believed that this device excels in the twisting mode because of the extremely even stress distribution it offers when simply compressed. As such, while each of the stent types shown in FIGS. 2A-3B may be employed in any of the systems described herein, the latter design may be preferred. Furthermore, the manner in which the "S" curves have been generated may be extended such that the analysis used to generate the as-cut (or near to as-cut) structures specifically accounts for the twisting the design will be subject to in certain variations of the invention. Specifically, physical or computational models may be employed in expanding a stent from an idealized compressed state to generate the desired uncompressed stent geometry.

However derived, in order that the stent pack cleanly when twisted, it may be desired to pre-curve its shape. That is to say, the stent may be configured so that when it is twisted, its members go from a pre-twisted shape to a straightened configuration as shown. The amount of shaping to account for hold-down twist, may be in the form of a simple bias or helix, S-curves or other shape(s).

Since each of the above stent designs account for problematic strain (and in the latter case actually uses the same to provide an improved compressed profile), very high compression ratios of the stent may be achieved from about 5× to about 10× or above. Moreover, they can be twisted a number of times to maintain a compressed delivery profile. The number of twists required for such action will vary depending on stent diameter and length. For a 28 mm stent sized to treat 3.0 mm vessels, between three and four twists may be desired. Similar diameter, shorter stents will require proportionally fewer rotations, as will generally smaller diameter stents.

Regardless of the design selected, it is noted that each of them exhibit significant foreshortening when expanding from a compressed profile. Essentially, the angle change of the struts relative to the central axis of the tubular body accounts for change in length. The amount of foreshortening experienced will, thus, depend on a combination of factors: strut length and angle as well as the number of repeating units within the design. The manner in which the resultant foreshortening is put to use in the present invention is elaborated upon below.

Before this discussion, however, it is noted that systems according to the present invention are advantageously sized to correspond to existing guidewire sizes. For example, the system may have about a 0.014 (0.36 mm), 0.018 (0.46 mm), 0.022 (0.56 mm), 0.025 (0.64 mm) inch crossing profile. Of course, intermediate sizes may be employed as well, especially for full-custom systems. Still further, it is contemplated that the system sizing may be set to correspond to French (FR) sizing. In that case, system sizes contemplated range at least from about 1 to about 2 FR, whereas the smallest known balloon-expandable stent delivery systems are in the size range of about 3 to about 4 FR. In instances where the overall device crossing profile matches a known guidewire size, they may be used with off-the-shelf components such as balloon and microcatheters.

At least when produced in the smallest sizes (whether in an even/standard guidewire or FR size, or otherwise), the system enables a substantially new mode of stent deployment in which delivery is achieved through an angioplasty balloon catheter or small microcatheter lumen. Further discussion and details of "through the lumen" delivery is presented in U.S. patent application Ser. No. 10/746,455 "Balloon Catheter Lumen Based Stent Delivery Systems" filed on Dec. 24, 2003 and its PCT counterpart US2004/008909 filed on Mar. 23, 2004, each incorporated by reference in its entirety.

In larger sizes (i.e., up to about 0.035 inch crossing profile or more), the system is most applicable to peripheral vessel applications as elaborated upon below. Yet, even in "small vessel" cases or applications (where the vessel to be treated has a diameter up to about 3.0 mm), it may also be advantageous to employ a stent delivery system sized at between about 0.022 to about 0.025 inch in diameter. Such a system can be used with catheters compatible with 0.022 and/or 0.025 inch diameter guidewires.

While such a system may not be suitable for reaching the very smallest vessels, this variation of the invention is quite advantageous in comparison to known systems in reaching the larger of the small vessels (i.e., those having a diameter of about 2.5 mm or larger). By way of comparison, among the smallest known over-the-guidewire delivery systems are the Micro-Driver™ by Medtronic and Pixel™ systems by Guidant. These are adapted to treat vessels between 2 and 2.75 mm, the latter system having a crossing profile of 0.036 inches (0.91 mm). A system described in U.S. Patent Publication No. 2002/0147491 for treating small vessels is supposedly capable of downsizing to 0.026 inch (0.66 mm) in diameter. Furthermore, because the core member of the subject device can be used as a guidewire (in one fashion or another) after stent delivery, the present invention offers further advantages in use as elaborated upon below.

As referenced above, it may be desired to design a variation of the subject system for use in deploying stents in larger, peripheral vessels, biliary ducts or other hollow body organs. Such applications involve a stent being emplaced in a region having a diameter from about 3.5 to 13 mm (0.5 inch). In which case, a 0.035 to 0.039 inch (3 FR) diameter crossing profile system is advantageously provided in which the stent expands (unconstrained) to a size between about roughly 0.5 mm and about 1.0 mm greater than the vessel or hollow body organ to be treated. Sufficient stent expansion is easily achieved with the exemplary stent patterns shown in FIGS. 2A/2B or 3A/3B.

Again, as a matter of comparison, the smallest delivery systems known to applicants for stent delivery in treating such larger-diameter vessels or biliary ducts is a 6 FR system (nominal 0.084 inch outer diameter), which is suited for use in an 8 FR guiding catheter. Thus, even in the larger sizes, the present invention affords opportunities not heretofore possible in achieving delivery systems in the size range of a commonly used guidewire, with the concomitant advantages discussed herein.

As for the manner of using the inventive system as optionally configured, FIGS. 4A-4L illustrate an exemplary angioplasty procedure. Still, the delivery systems and stents or implants described herein may be used otherwise—especially as specifically referenced herein.

Figure 4A:
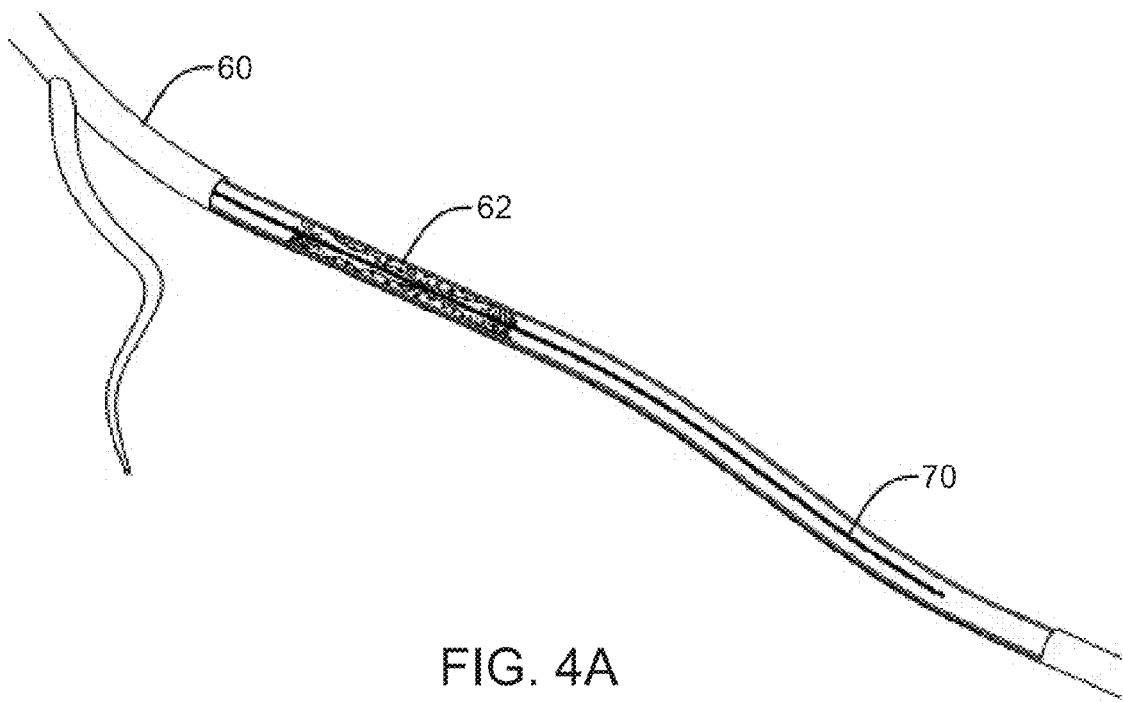
FIGS. 4A-4L illustrate stent deployment methodology to be carried out with the subject delivery guide member.
Figure 4B:
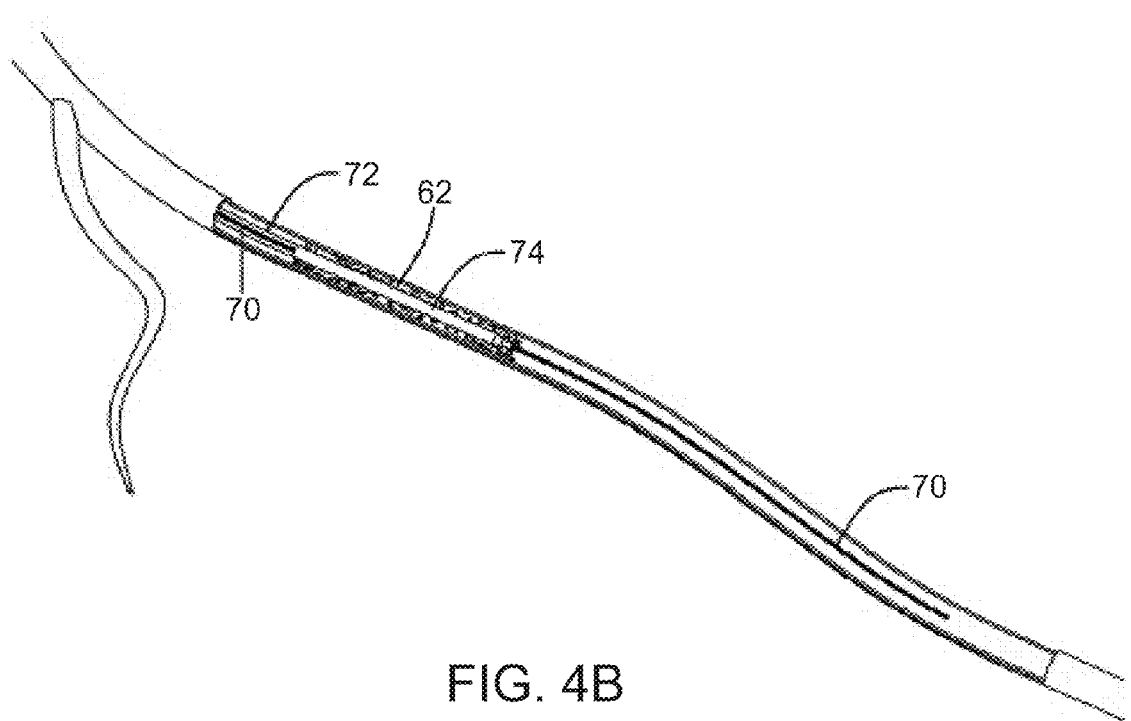

Turning to FIG. 4A, it shows a coronary artery 60 that is partially or totally occluded by plaque at a treatment site/lesion 62. Into this vessel, a guidewire 70 is passed distal to the treatment site. In FIG. 4B, a balloon catheter 72 with a balloon tip 74 is passed over the guidewire, aligning the balloon portion with the lesion (the balloon catheter shaft proximal to the balloon is shown in cross section with guidewire 70 therein).

Figure 4C:
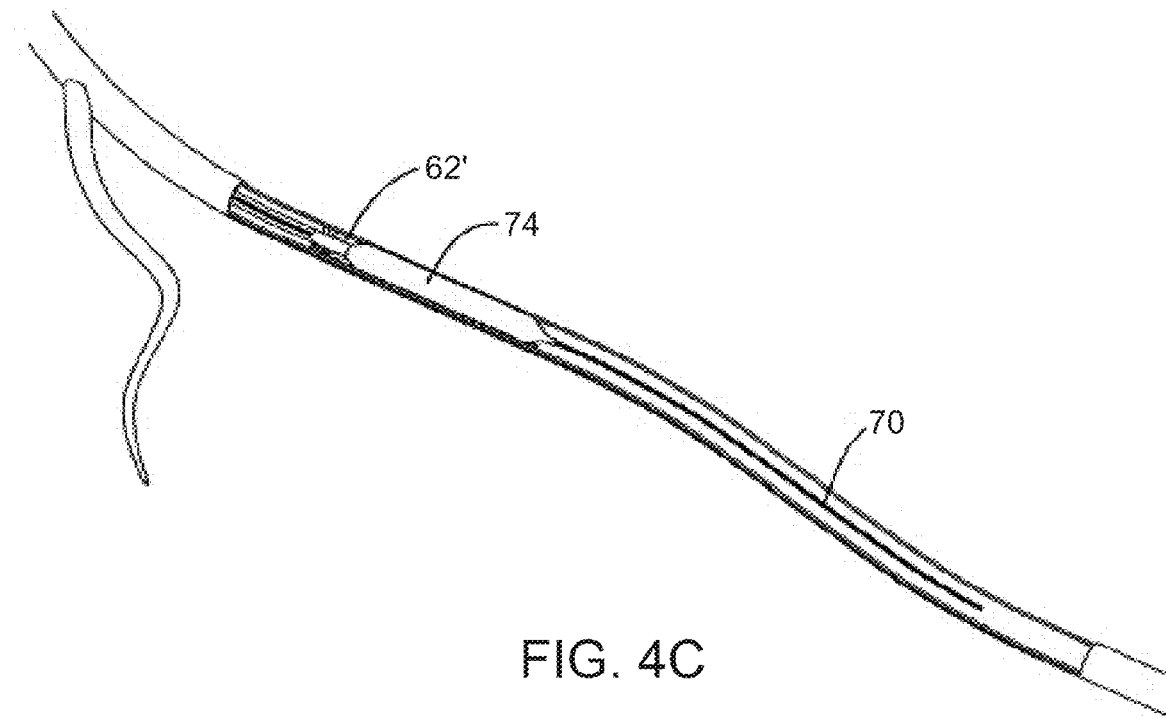

As illustrated in FIG. 4C, balloon 74 is expanded (dilatated or dialated) in performing an angioplasty procedure, opening the vessel in the region of lesion 62. The balloon expansion may be regarded as "predilatation" in the sense that it will be followed by stent placement (and optionally) a "postdilatation" balloon expansion procedure.

Figure 4D:
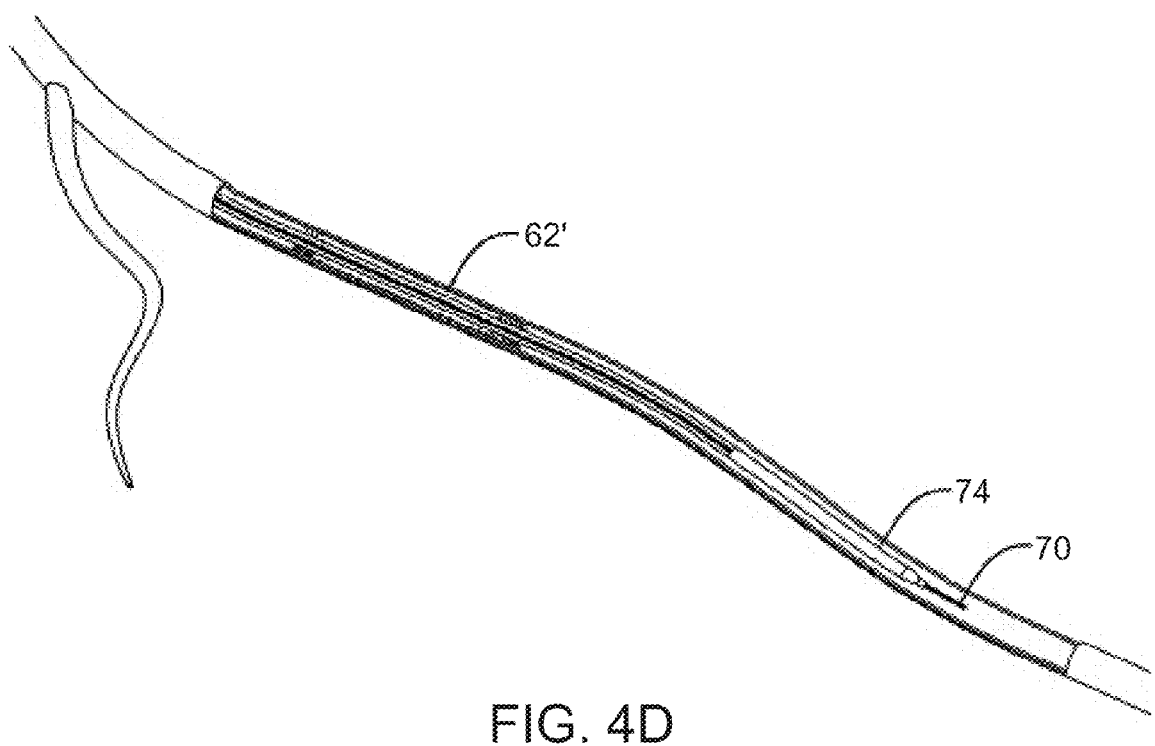
Figure 4E:
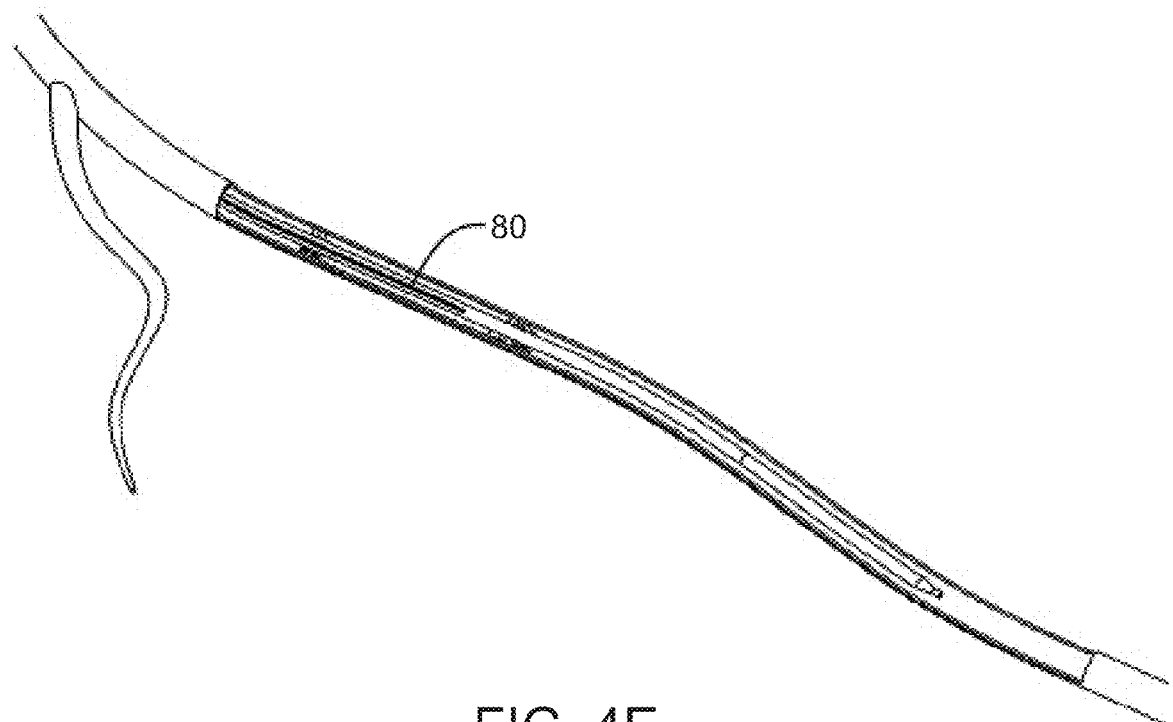
Figure 4F:
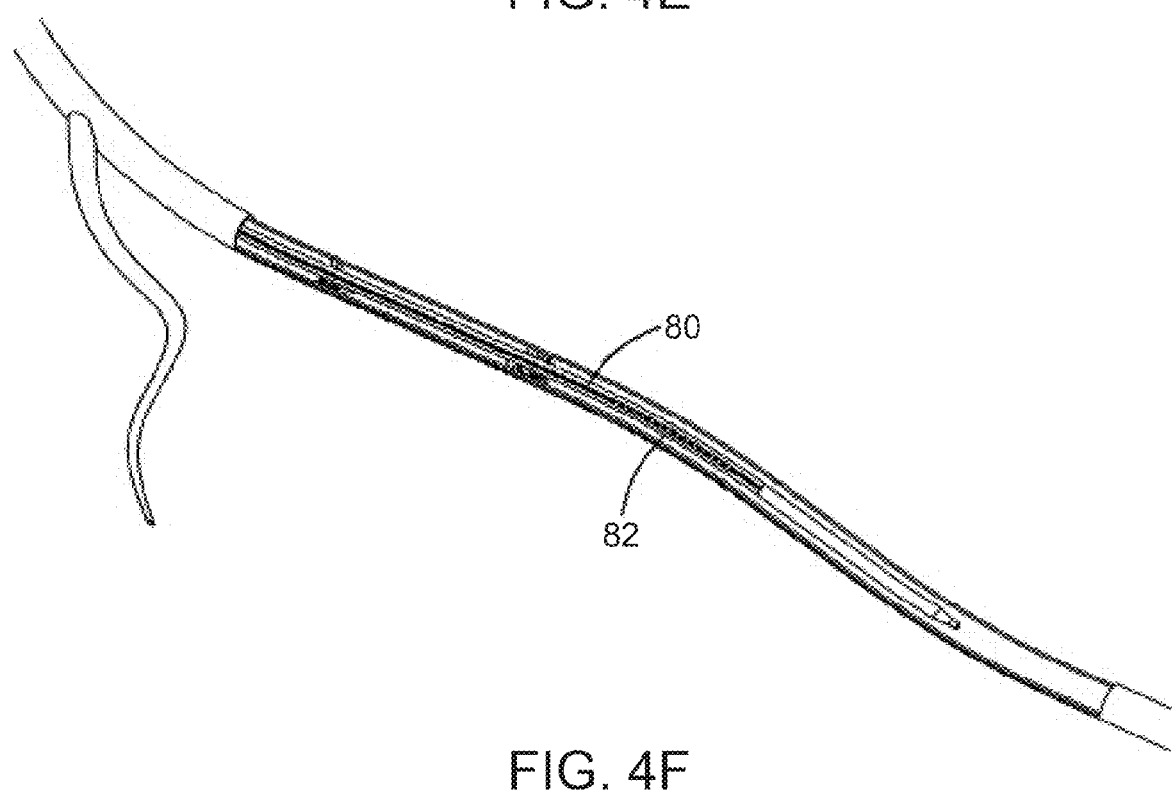

Next, for compatible systems (i.e., systems able to pass through a balloon catheter lumen) the balloon is at least partially deflated and passed forward, beyond the dilate segment 62' as shown in FIG. 4D. At this point, guidewire 70 is removed as illustrated in FIG. 4E. It is exchanged for a delivery guide member 80 carrying stent 82 as further described below. This exchange is illustrated in FIGS. 4E and 4F.

However, it should be appreciated that such an exchange need not occur. Rather, the original guidewire device inside the balloon catheter (or any other catheter used) may be that of item 80, instead of the standard guidewire 70 shown in FIG. 4A. Thus, the steps depicted in FIGS. 4E and 4F (hence, the figures also) may be omitted.

Alternatively, the exchange of the guidewire for the delivery system may be made before the dilatation step. Yet another option is to exchange the balloon catheter used for predilatation for a fresh one to effect postdilatation.

Figure 4G:
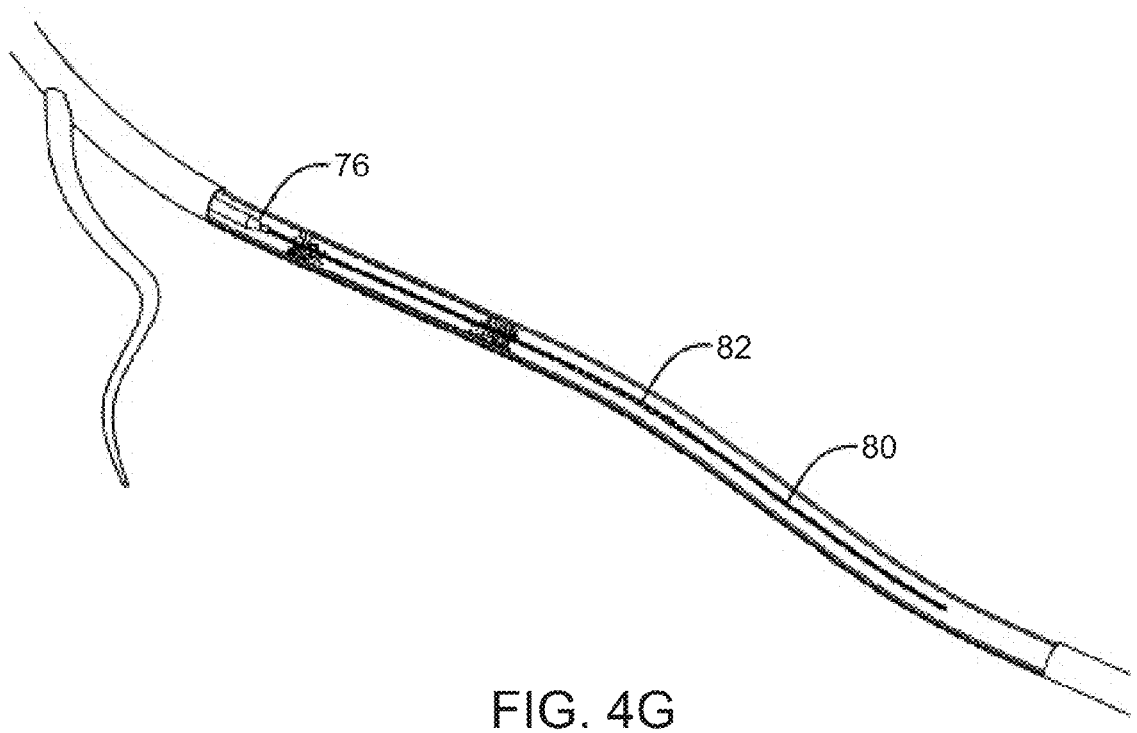
Figure 4H:
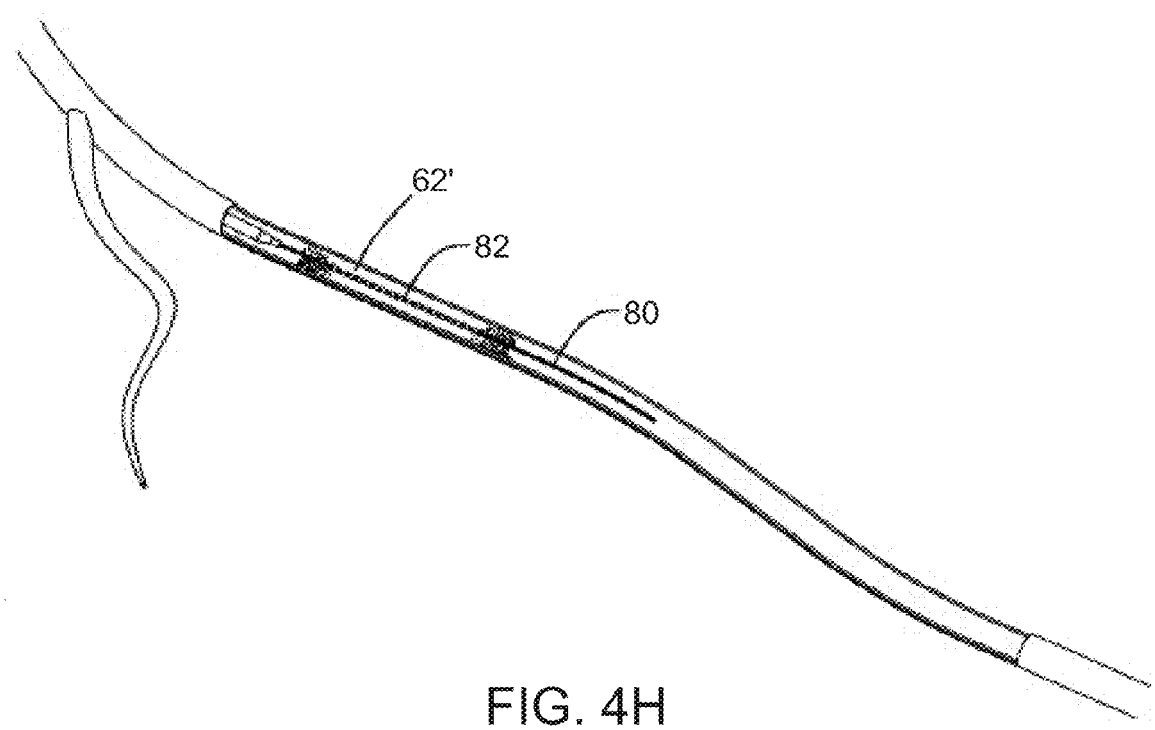

In addition, there may be no use in performing the step in FIG. 4D of advancing the balloon catheter past the lesion, since such placement is merely for the purpose of avoiding disturbing the site of the lesion by moving a guidewire past the same. FIG. 4G illustrates the next act in either case. Particularly, the balloon catheter is withdrawn so that its distal end 76 clears the lesion. Preferably, delivery guide 80 is held stationary, in a stable position. After the balloon is pulled back, so is delivery device 80, positioning stent 82 where desired. Note, however, that simultaneous retraction may be undertaken, combining the acts depicted in FIGS. 4G and 4H. Whatever the case, it should also be appreciated that the coordinated movement will typically be achieved by virtue of skilled manipulation by a doctor viewing one or more radiopaque features associated with the stent or delivery system under medical imaging.

Figure 4I:
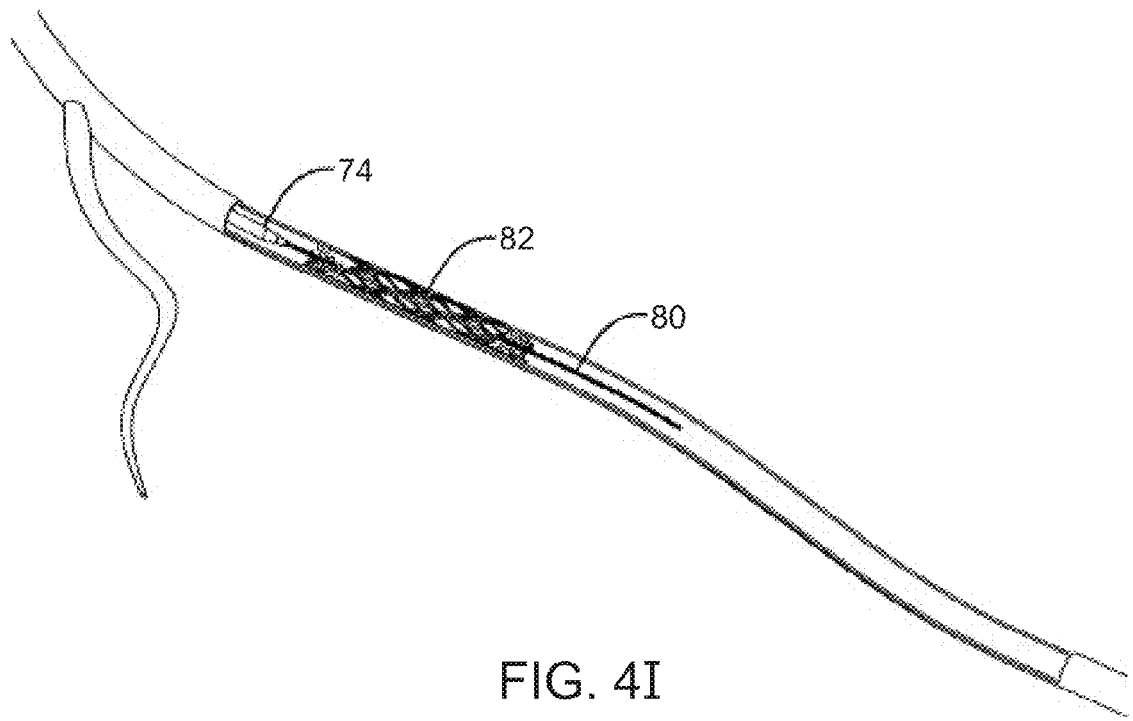
Figure 4J:
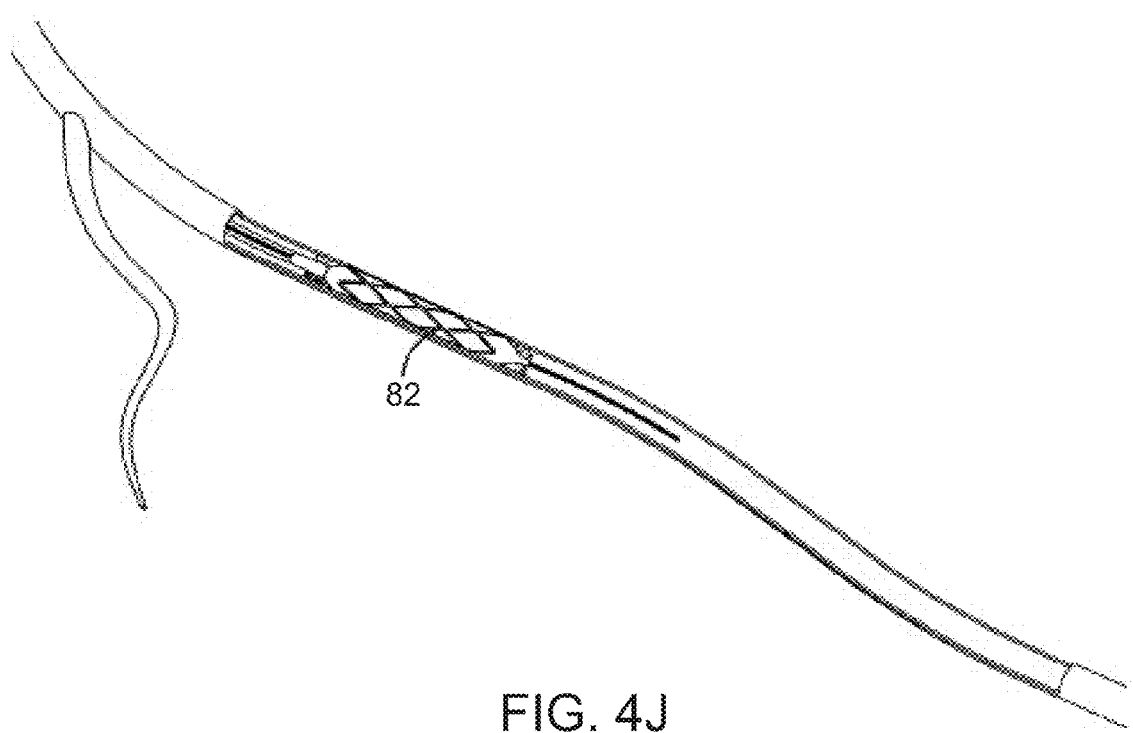
Figure 4K:
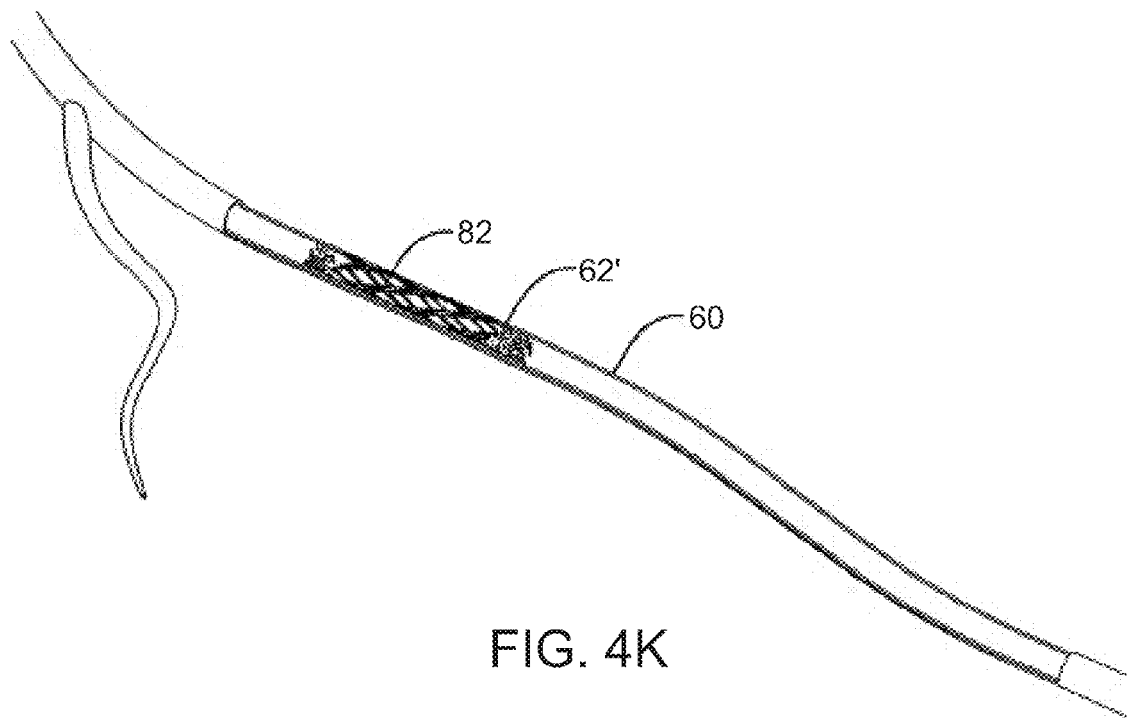

Once placement of the stent across from dilated segment 62' is accomplished, stent deployment commences. The manner of deployment is elaborated upon below. Upon deployment, stent 82 assumes an at least partially expanded shape in apposition to the compressed plaque as shown in FIG. 4I. Next, the aforementioned postdilatation may be effected as shown in FIG. 4J by positioning balloon 74 within stent 82 and expanding both. This procedure may further expand the stent, pushing it into adjacent plaque—helping to secure each.

Figure 4L:
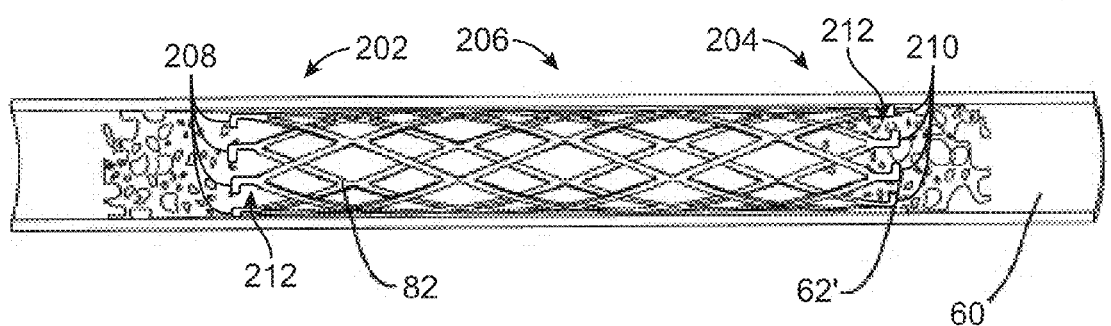

Naturally, the balloon need not be reintroduced for postdilatation, but it may be preferred. Regardless, once the delivery device 80 and balloon catheter 72 are withdrawn as in FIG. 4K, the angioplasty and stenting procedure at the lesion in vessel 60 is complete. FIG. 4L shows a detailed view of the emplaced stent and the desired resultant product in the form of a supported, open vessel.

Furthermore, it is to be recognized that the subject invention may be practiced to perform "direct stenting." That is, a stent may be delivered alone to maintain a body conduit, without preceding balloon angioplasty. Likewise, once one or more stents are delivered with the subject system (either by a single system, or by using multiple systems) the post-dilatation procedure(s) discussed above are merely optional. In addition, other endpoints may be desired such as implanting an anchoring stent in a hollow tubular body organ, closing off an aneurysm, delivering a plurality of stents, etc. In performing any of a variety of these or other procedures, suitable modification will be made in the subject methodology. The procedure shown is depicted merely because it illustrates a preferred mode of practicing the subject invention, despite its potential for broader applicability.

Returning to FIG. 4L, the stent 82 comprises a near end 202, a far end 204 and a support structure 206 extending therebetween. The support structure 206 is configured to reduce in diameter upon rotation of the near end 202 relative to the far end 204. The stent 82 further comprises projections 212 that allow the stent to be retained upon the delivery system when in a twist-down or compressed state. The projections 212 comprise a near mating portion 208 and a far mating portion 210 that permit retention of the prosthesis 82 on a delivery system when the ends are rotated relative to one another.

A given implant may have a number of projections 212, each having various shapes rather than having a single configuration. Typically, at least two projections will be provided on each side of the stent. When not every stent crown is capped by a projection, the projections are advantageously spaced substantially equally about the perimeter of the stent to evenly distribute loads upon the stent. In which case, the projections may be aligned with one another along the axis of the stent as shown in FIG. 4L or staggered about its axis of the stent. More typically, each crown will terminate with a projection and mating features. In this manner, the stent can be fully constrained without members tending to lift-off the delivery guide in a pure twisting mode of diameter reduction for delivery. Still further, it is contemplated that the number of crowns may be reduced by taking out adjacent arm sections to turn what was a four-crown design on each end into a two-crown design. In this way, fewer projections can be used, while still providing one for every full cell at each end of the stent.

The projections may vary in length, especially depending on the form of interface or mating portion they carry or form. The projections advantageously have a length that allow for efficiently transitioning or transferring the twisting load to the stent while occupying minimal space. Though not necessarily excluded from the invention, projections longer than about one cell's length may have a tendency either warp or twist about the delivery device body in attempted use. This feature can introduce undesirable sizing effects and/or difficulty in handling.

Figure 5:
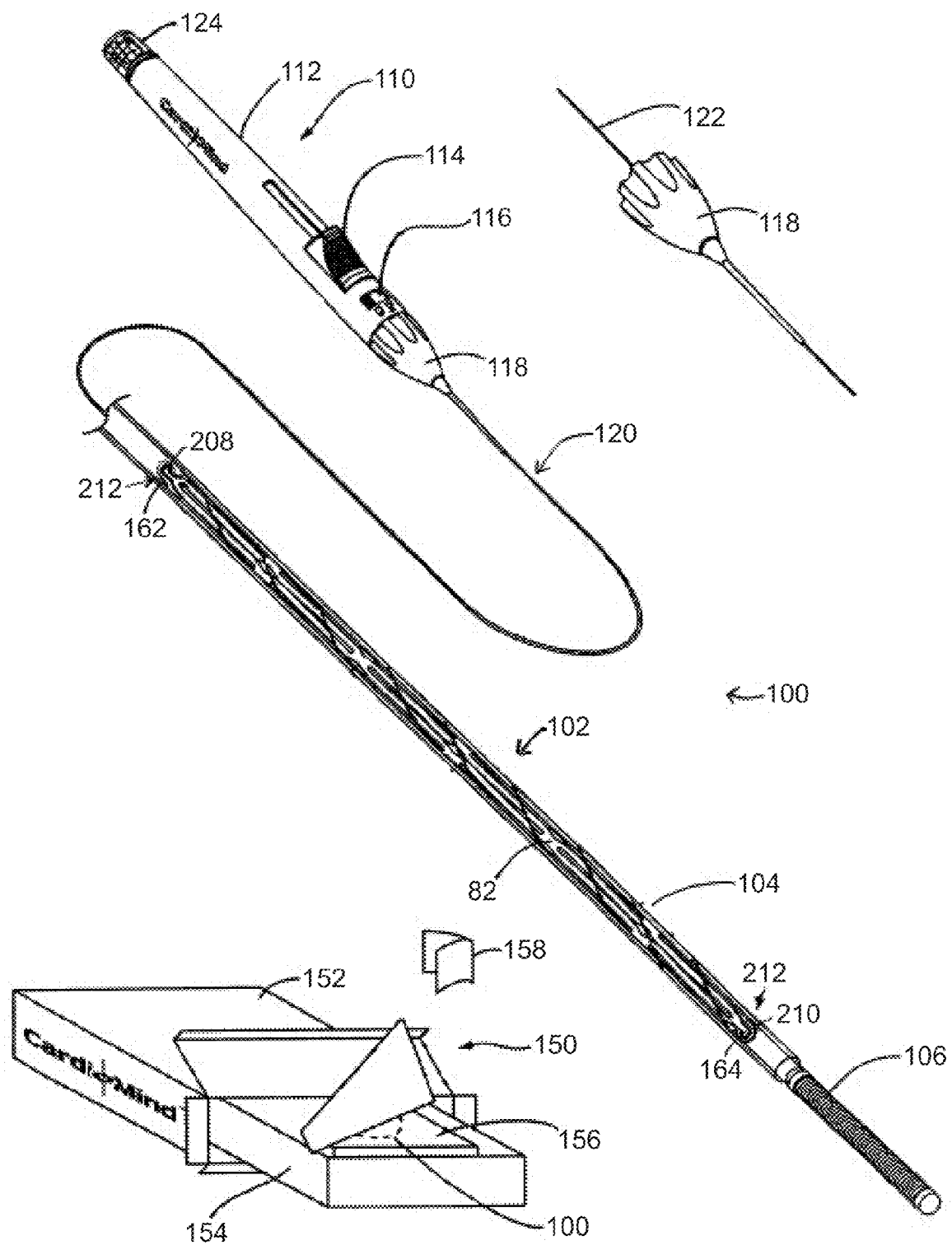
FIG. 5 provides an overview of a delivery system incorporating a tubular member according to the present invention.

Turning to FIG. 5, the mating portions 208, 210 of stent 82 have a shape that nests within seats 162, 164 of the system 100. The projections 212 may comprise shapes including, but not limited to an "L" shape, "T" shape, "V" shape, circular, rectangular, square, polygonal, diamond, triangular, elongate, and slotted projections 212 as the mating portions. In essence, the projections may take any number of shapes so long as they retain the stent in its twist-down state upon the delivery system. Furthermore, the projections 212 on a single stent 82 are not required to be the same shape. Instead, the shapes of the projections 212 may vary from each side of the stent. Furthermore a projection may have a distinct shape from an adjacent projection.

In any case, there will be at least a sufficient number of projections 212 extending from each end of the prosthesis 82 to balance the force required to maintain the prosthesis 82 in a reduced diameter upon twisting. For smaller designs (i.e., delivery systems with 0.014 to 0.016 inch crossing profiles) in certain systems, as few as two mating features may be provided on each side of the implant. With an increased compressed size, space is made available for more projections/mating features.

The stent 82 may be secured on the delivery system by twisting (or at least partially twisting) the stent 82 prior to loading on the delivery system. Alternatively, the expanded stent 82 may be placed over a delivery system core member, and the ends of the stent 82 then twisted to constrict the stent 82 about the delivery system. Further, appropriate fixturing or preloading into a sleeve or multiple sleeve portions that may be twisted relative to one another may assist in loading of the stent about the delivery system as described in U.S. patent application Ser. No. 11/265,999, entitled "Indirect-Release Implant Delivery Systems," incorporated by reference for this purpose. Naturally, the approach described there may be modified to accommodate differences between the system referenced therein and those of the present invention.

As for a general overview of the subject delivery systems as provided in FIG. 5, delivery system 100 is shown with a stent carried at a distal end 102 of an elongate body in a collapsed configuration. In this example the twisted stent is overlaid by a full-length sheath 104. With the stent in a twisted configuration, at least initial motion of the sheath is eased. In other words, because the stent is held in an at least a partially compressed configuration by the twist imparted thereto, the stent does not push or strain against the sheath to the same degree (or at all), thereby reducing friction at the interface. Thus, the overlaying sheath may be removed (or at least the initial movement of the sheath) more easily relative to a simple-sheath type delivery system. For examples in which the key/seat portions are rotatably manipulatable relative to one another (for example by a handle knob and as in other examples elaborated below) to hold the stent in a collapsed configuration, the sheath may be fully withdrawn from the at least partially twisted stent. As compared to a sheathless-twistdown as provided below, an additional safety margin may be offered by the overlying sheath.

As elaborated upon below, alternative stent hold-down features or means may be provided in accordance with the present invention. Regardless, the delivery guide preferably includes/comprises a flexible atraumatic distal tip 108 of one variety or another.

On the other end of the delivery device, a handle 110 may be provided. A body 112 of the handle may include one or more of a lever or slider 114 or other means (such as a trigger, knob or wheel) for actuating optional sheath/restraint or core member withdrawal. The delivery device handle may include a lock 116 to prevent inadvertent actuation. Similarly, handle 110 may include various safety or stop features and/or ratchet or clutch mechanisms to ensure one-way actuation. The handle 110 further includes a knob 124 that permits twisting/untwisting of the stent. Of course, other alternative interface means may be provided to effect such action.

Furthermore, a removable interface member 118 may be provided to facilitate taking the handle off of the delivery system proximal end 120. The interface may be lockable with respect to the body and preferably includes internal features for disengaging the handle from the delivery guide. Once accomplished, it will be possible to attach or "dock" a secondary length of wire 122 on the delivery system proximal end, allowing the combination to serve as an "exchange length" guidewire, thereby facilitating changing-out the balloon catheter or performing another procedure. Alternatively, a core member within the system may be an exchange-length wire.

FIG. 5 also shows packaging 150 containing at least one coiled-up delivery system 100. Packaging may include one or more of an outer box 152 and one or more inner trays 154, 156 with peel-away coverings as is customary in medical device product packaging. Naturally, instructions for use 158 may also be provided. Such instructions may be printed product included within packaging 150 or be provided in connection with another readable (including computer-readable) medium. The instructions may include provision for basic operation of the subject devices and associated methodology.

In support of such use, it is to be understood that various radiopaque markers or features may be employed in the system to 1) locate stent position and length, 2) indicate device actuation and stent delivery and/or 3) locate the distal end of the delivery guide. As such, various platinum (or other radiopaque material) bands or other markers (such as tantalum plugs) may be incorporated into the system. Especially where the stent employed may shorten somewhat upon deployment, it may also be desired to align radiopaque features with the expected location (relative to the body of the guide member) of the stent upon deployment. For such purposes, radiopaque features may be set upon the core member of the delivery device proximal and distal of the stent.

While FIG. 5 illustrates a full-size delivery system, a number of the following figures illustrate detail views of the far or distal end 102 of such a system 100, that depict a number of approaches for releasably securing a stent for delivery according to the present invention. The device features are typically incorporated into complete systems and may be used in the manner described, as well as others as may be apparent to those with skill in the art.

Figure 6:
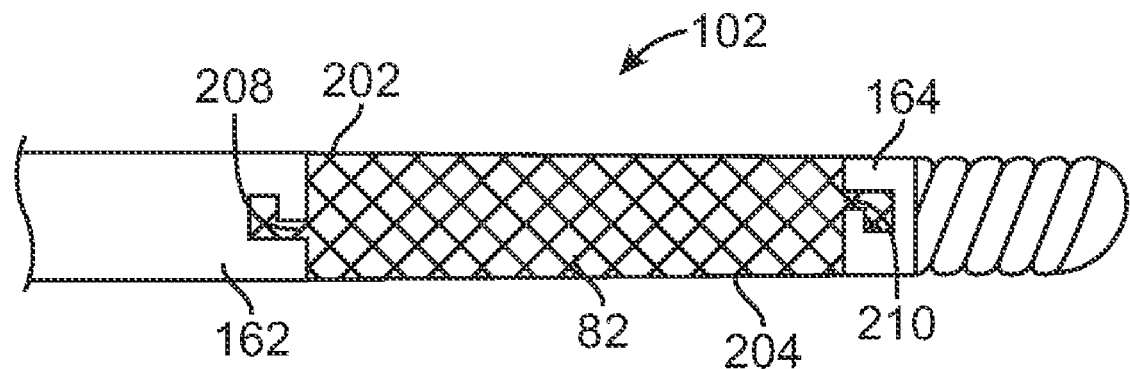
FIG. 6 illustrates an example of a variation of a delivery system of the present invention without the prosthesis (or in an unloaded configuration)

Accordingly, FIG. 6 illustrates the far end 102 of a delivery system end including a prosthesis (e.g., a stent) 82 placed about an inner member underlying the stent. As referenced above, prosthesis 82 comprises a proximal/near end 202, a distal/far end 204 and a support structure 206 extending therebetween. As noted above, support structure 206 comprises a mesh, lattice, woven, or other similar structure that reduces in diameter upon rotation of near end 202 relative to far end 204. Such a structure offers excellent strength and uniform support when expanded, yet does not foreshorten to the degree that a coil stent does in expansion from a compressed configuration.

Prosthesis 82 further comprises projections that permit retention of the prosthesis 82 on delivery system 100 when the ends are rotated relative to one another. The projections shown comprise a near key, interface or mating portion 208 and a far key, interface or mating portion 210. The various structures described for the seats and mating portions that interface or compliment one another to retain the stent to the elongate member may be regarded as the various means for retaining the prosthesis to the elongate member disclosed herein. An exemplary representation of the stent-side mating/interface features is presented in FIGS. 8A-8D.

Complimentary seats are shown in the various delivery guide portions. For example, In FIGS. 6 and 7 respective seats 162, 164 of system 100 receive hook or L-shaped mating portions 208 and 210 of the type shown in FIG. 8A.

Figure 7:
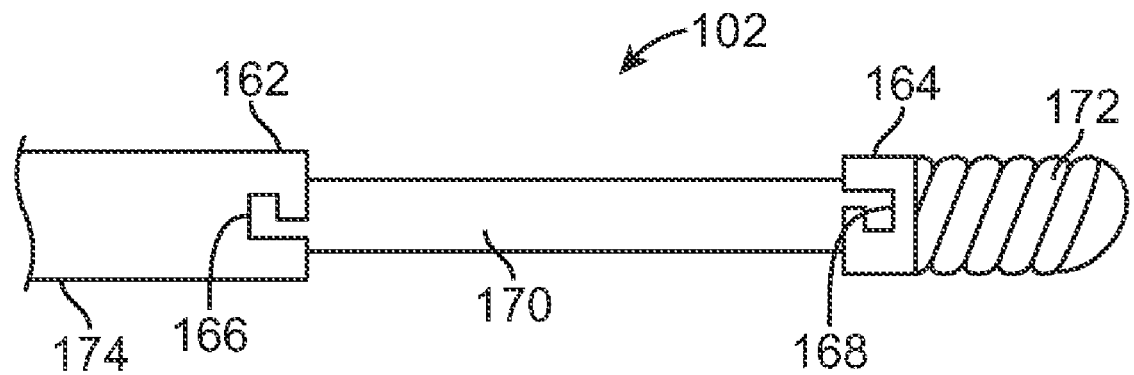
FIG. 7 illustrates an example of a stent for use with the present invention.

FIG. 7 depicts the variation of the system 100 shown in FIG. 6 without the prosthesis so as to better illustrate the various elements. As illustrated, an inner member 170 extends through at least a portion of the system 100. It should be noted that the inner member 170 may comprise a coiled guide wire, a core wire, or other member that extends through the entire system 100 or at least a portion of the system. The distal end of the core member 170 comprises the distal end of the system 100 and may include a coil tip 172 or other atraumatic tip for navigation through delicate body structures (e.g., the peripheral vasculature, or other vasculature, ducts passageways, etc.). The core member 170 includes a section for mounting the prosthesis which may be tapered from a remainder of the core member. In addition, to accommodate a coil tip 172, the core member 170 may include one or more additional tapered segments that permit tuning system flexibility and/or construction of a compliant coil tip 172.

FIG. 7 also shows the far seat 164 associated with the core member 170. The seat comprises a geometry 168 shaped to receive the far mating portion of the prosthesis. The far seat 164 may be integral with the core member 170 or may be affixed to the core member.

The near seat 162 includes a receptacle form 166 that is shaped to receive the near mating portion of the prosthesis. As illustrated, the near seat 162 is formed from the distal end of an outer member 174 that extends over at least a portion of the core member 170. In this variation, the core member 170 may be moveable relative to the outer member 174. In one variation, the core member 170 may be rotatable relative to the outer member 174. Alternatively, or additionally, the core member 170 and the outer member 174 may be axially moveable relative to each other. Such features are useful to retain and/or deploy the prosthesis as discussed below.

The core member 170 may be elongate and have a comparatively small effective diameter. It has the function of permitting delivery of the prosthesis to a selected site and supporting the prosthesis in a collapsed form during positioning and implantation. The core member may be solid, or may have a lumen extending therethrough, depending on such factors as the degree of flexibility required, the type of associated release mechanism, the constituent material, and the like. The tip of the core member (i.e., the distal end of the delivery system) may include an atraumatic tip and be tapered and/or straight, curved, or J-shaped, depending on factors such as physician preference the anatomy of the tubular organ or region of interest, degree of stiffness required, and the like.

As noted herein, the subject delivery system 100 employs a prosthesis 82 that reduces in diameter when the ends of the prosthesis are rotated relative to each other in a first direction. Accordingly, when the mating portions 208, 210 of the prosthesis are nested with the near and far seats 162, 164, the near and far ends 202, 204 of the prosthesis 82 are restrained or prevented from rotating in a second direction to expand the prosthesis until desired by the medical practitioner. To assist in restraining the prosthesis, the core member 170 may be releasably locked relative to the outer member 174 to prevent relative movement. Therefore, when desired, the core member 170 and outer member 174 may be released so that the prosthesis may untwist to expand in diameter (e.g., where the prosthesis self expands). In some variations of the invention, the medical practitioner may assist in expanding the prosthesis by rotating the core member 170 relative to the outer member 174.

The ability to axially move the outer member 174 relative to the core member 170 may assist in restraining or assist in deploying the prosthesis. For example, variations of the invention described herein may rely upon moving the far seat 164 distally relative to the near seat 162 to disengage the projections of the prosthesis from the seats. Alternatively, when the projections are hook or L-shaped, movement of the far seat 164 distally relative to the near seat 162 causes axial "extension" of the prosthesis which counteracts any internal bias within the prosthesis to expand. It should be noted that movement of the seats may be accomplished in any number of ways. For example, the core member may advance relative to the near seat. Alternatively, the near seat (or outer member) may be withdrawn relative to the distal seat.

As mentioned above, the near and far seats 162, 164 each define a receptacle form 166, 168 shaped to receive the mating portions 208, 210 of the prosthesis. The receptacle geometries may comprise a plurality of openings (as illustrated) shaped to receive one or more projection(s) of the prosthesis. The openings may extend partially to a certain depth (i.e., forming a pocket). Alternatively, the openings may extend through the entire member. As noted above with respect to the projections, the shapes of the openings may include, but are not limited to: "L" shapes, "T" shapes, "V" shapes, circular, rectangular, square, polygonal, diamond, triangular, and slot shapes.

Figure 8A:
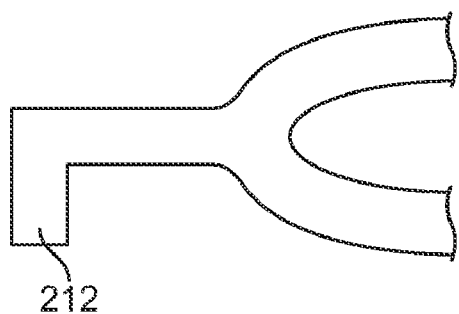
FIGS. 8A-8F illustrates various projections of the mating portions of stents in accordance with the present invention.
Figure 8B:
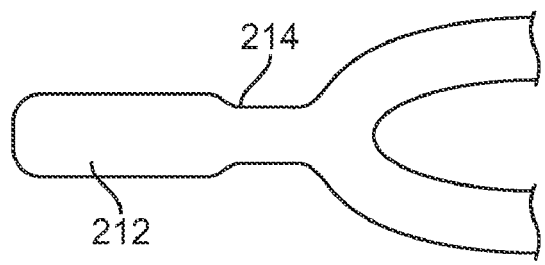
Figure 8C:
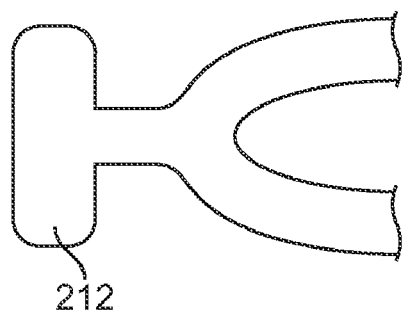
Figure 8D:
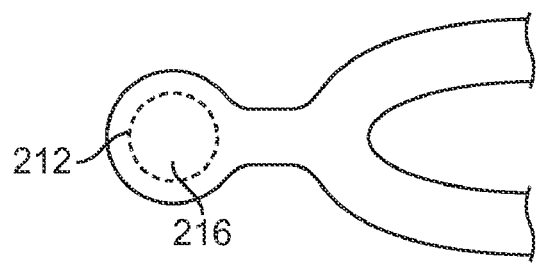
Figure 8E:
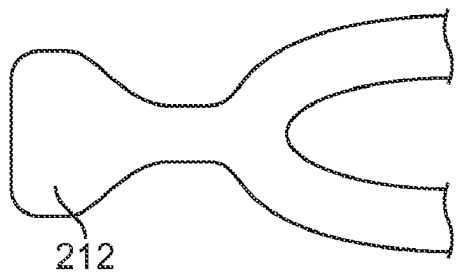

FIGS. 8A-8F, illustrates variations of projections 212 for use in the present invention. As illustrated FIG. 8A shows an "L" shaped projection. FIG. 8B illustrates a rectangular shaped projection 212. It is noted that FIG. 8B also illustrates an axially extending discrete projection 212 as having optional notches 214. Such features can assist by offering additional compliance in compressing the adjacent struts 52 of the stent through material removal at their junction with the projection. FIG. 8C illustrates a "T" shaped projection 212. FIGS. 8D and 8E illustrates circular shaped projections and "V" shaped projections respectively. FIG. 8D also illustrates an example of radiopaque marker 216 (e.g., a tantalum plug). The projections may align with the struts/cell geometry, or they may be offset therefrom. By offsetting the entire projection and/or portion(s) thereof (e.g., as in the FIG. 8A variation) the features may be situated to more advantageously counteract any tendency of the ends of the stent or the projections themselves to lift off the delivery guide body components due to the twisting imparted to the same.

Figure 8F:
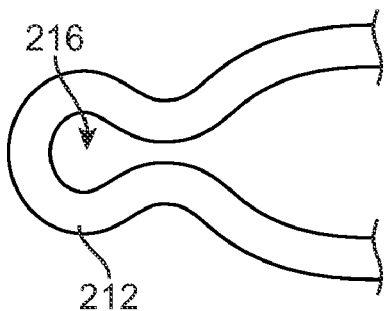

Alternatively, region 216 may be left open in order to provide a mating portion defined by negative space. In such fashion, the mating portion of the projection comprises the receptacle for receiving a pin or another member (the seating interface on the delivery system). A similar approach is shown in FIG. 8F, but negative space 216 is provided as a portion of the stent cell geometry in a "C" shaped form. Irregardless of construction, various male or female interface approaches may be employed. Indeed, the mating portions formed on or by the projections may have any number of different shapes so long as they are conducive to interfacing with complimentary delivery system hardware.

In addition, a single prosthesis or stent may have any number of projections of various shapes so long as the projections do not unacceptably interfere or contact on another when compressing the stent. Accordingly, it is understood that the shape and configuration of the projection may vary for any number of factors (e.g., the particular application, the size of the stent, the tortuousity of the vasculature, etc.). As a result, the projections may comprise any hook, prong, opening, socket, key, grasper, tooth, bar or slot shaped configuration (whether the shape is nearly planar or significantly extends in three dimensions) in addition to those shapes discussed herein. In accordance with the above, it follows that the corresponding seating features will be selected to accommodate the shape of the respective projection.

In any case, the shapes of the projections will be selected so as not to create undue risk of injury to the patient. For example, for vascular applications, the shape of the projections must be chosen so as not to create undue trauma to the vessel wall. On the other hand, non-vascular applications may not present the same risks. Accordingly, the design of the projections may be more aggressive in stents intended for such applications.

As discussed above, the invention contemplates the use of one or more sleeves completely covering the implant as shown in FIG. 5, or set about the near and/or far end of the stent to assist in retention of the stent about the system. Alternative variations of the delivery system 100 may employ the stent without any additional sleeves or restraints as shown in FIG. 6 and others below, including the variation shown in FIG. 9A.

Figure 9A:
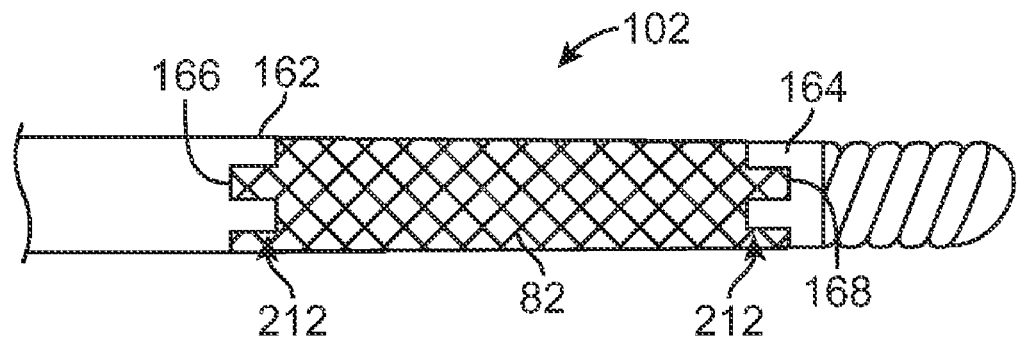
FIGS. 9A-9C depicts variations of the implant delivery system.

In FIG. 9A, delivery system end 102 employs elongate projections 212 nested in the near and far seats 162, 164 that have "slot-shaped" openings 166, 168 to accommodate the elongate projections. The prosthesis or stent 82 may be deployed by rotating the far seat 164 relative to the near seat 162 to untwist the stent 82, allowing the projections 212 to slide or release (radially outward) from the seats. Alternatively, or in combination, the near and far seats 162, 164 may be moved away from each other to free a self-expanding stent 82 from restraint. In such a case, the stent 82, once removed from the restraints, untwists to expand.

Figure 9B:
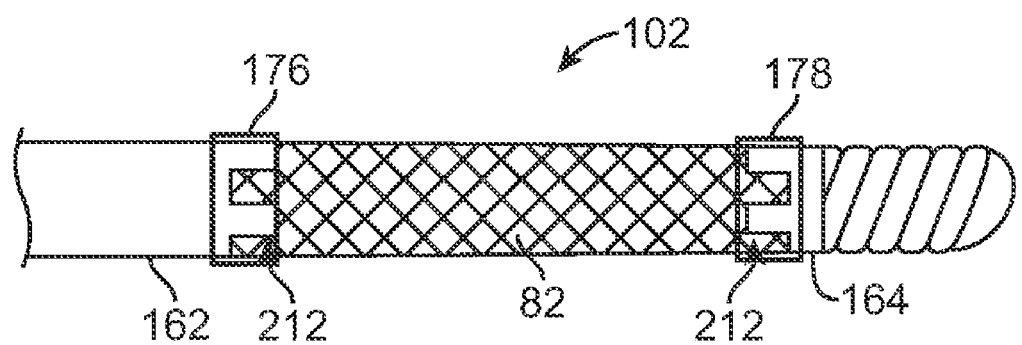

FIG. 9B illustrates the system interface approach taught in FIG. 9A with the addition of at least one of a near and far (or first and second) sleeves or bands 176, 178. It should be noted that for clarity the sleeves are drawn as being clear. However, the sleeves may be clear, opaque, radiolucent, or otherwise visible. The sleeves may be desired in order to provide an additional level of safety from inadvertent release of the stent. The sleeves insure that projections 210 cannot lift out of their respective seats (e.g., in extreme tortuousity). Rather, the stent can only be released upon untwisting of the stent (causing foreshortening and pull-out) or by user separation of the seats by manipulation of delivery system 100.

The release may occur simultaneously between the ends, or it may be staged. To stage the release when using elongate members that pull out of their respective seats, the length of the projections may vary from one side of the implant to the other. Assuming an equal rate of withdrawal, this can cause the shorter one(s) to withdraw relatively sooner, leaving at least a portion of the longer members engaged. Alternatively, the longer one(s) may remain stationary due to higher static friction than the shorter one(s), while the shorter members are first withdrawn. In either case, the remaining side of the implant may be released by manipulating the position of the delivery system (e.g., moving it proximally to release a proximal side or distally to release a distal side). Alternatively, expansion of the stent from the first side released can cause foreshortening and/or an angle change at the second end of the stent causing it to self-deploy in sequential fashion. In yet another approach in support of sequential end release, the projections may differ in shape from one side to the other such that one side is retained by an interlocking interface while the other is withdrawn. Such systems are discussed further below.

Figure 9C:
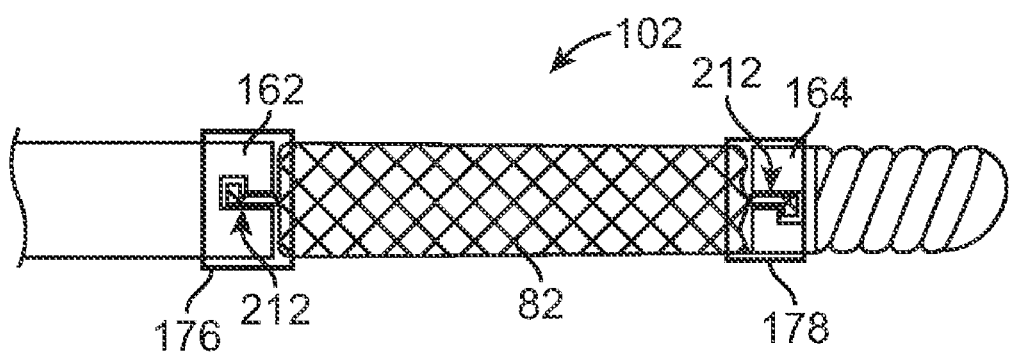

FIG. 9C illustrates another variation optionally employing a substantially different mode of implant release. In this variation, the system end 102 comprises near and far seats 162, 164 having near and far openings 166, 168 that each have "L" shaped openings. The stent 82 comprises corresponding "L" shaped projections. To deploy the stent 82, the near and far seats 162, 164 are rotated relative to one another causing the stent 82 to expand at its center. This action may cause the mating portions to lift out of their nesting regions. Alternatively, once the center of the stent 82 expands by untwisting alone, the practitioner may move the seats together to force the projections to lift out of the seats and deform cap or sleeve portions 176, 178.

Accordingly, the sleeves or caps in the variation show in FIG. 9C must be flexible enough or friable/splitable to allow the mating portions to lift out. Stated otherwise, the sleeves 176, 178 will be adapted to allow the projections to leave the openings. As the stent foreshortens, the projections will typically retract past the sleeve portions 176, 178. In contrast, note that the sleeves or caps 176, 178 in the variation of the invention in FIG. 9B may be either flexible or rigid since their deformation is not required to release the mating portions which are not initially axially locked.

Figure 10A:
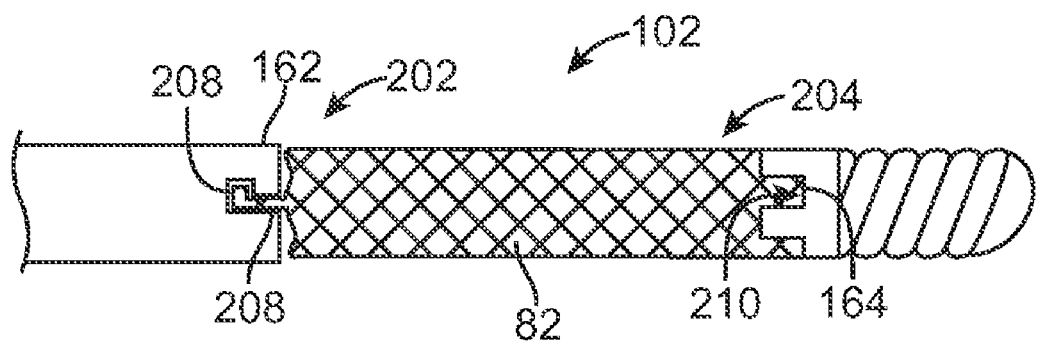
FIG. 10A illustrates an additional variation of an implant delivery system.

FIG. 10A illustrates a variation of a delivery system according to the present invention with an end 102 adapted to employ a stent 82 with projections having different configurations on either end of its body. In the illustrated example, the near and far seats 162, 164 seat a stent 82 having projections 212 at a far end 204 that are elongate and projections 212 at a near end 202 that are hooked (having a hook portion extending out-of-plane) or "L" shaped. Stent deployment in this variation of the invention occurs as discussed above via axial movement of the far seat 164 (or core member) away from the near seat 162 to disengage the projections 212 at the far end 204 of the stent while those at the near end 202 remain engaged with the near seat 162. Then, once released from the state of tension/torsion, the near keys/engagement members release from the seats. Though expansion of the stent may occur nearly instantaneously, it still results in a distal-to-proximal deployment as is generally desired.

Figure 10B:
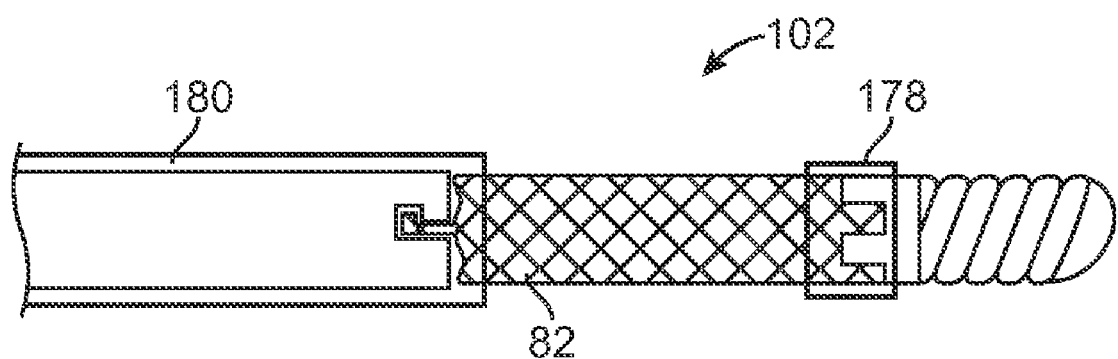
FIG. 10B illustrates an additional variation of an implant delivery system having a moveable sheath over the proximal portion of the delivery system.

FIG. 10B illustrates a system having an end 102 similar to that of FIG. 10A, with the addition of a sleeve 180 that is slidable over a portion of the system 100. In this variation, the system also includes a far sleeve or cap 178. However, it is contemplated that the sleeve 180 may be extendable over the entire length of the stent 82 to serve as a sheath without the use of such a sleeve or cap as in a system described above in connection with FIG. 5. The sheath may comprise a flexible polymeric material or be otherwise constructed.

With the device shown in FIG. 10B, deployment occurs by moving the proximal seat (together with sleeve 180) relative to the distal seat 164 to first release the slidable projections 212 from far seat 164. At this point, the stent unwinds and expands. Then, sleeve or sheath 180 is withdrawn to release the projections from proximal seat 162. (In this instance, at least the distal end of sleeve is such that it can hold the keyed features without their automatic release as in the variation of the invention in FIG. 9C.) In such a configuration, sleeve or sheath 180 offers a remotely actuatable "saftey" ensuring so that the stent is prevented from deploying until desired by the medical practitioner.

Figure 11A:
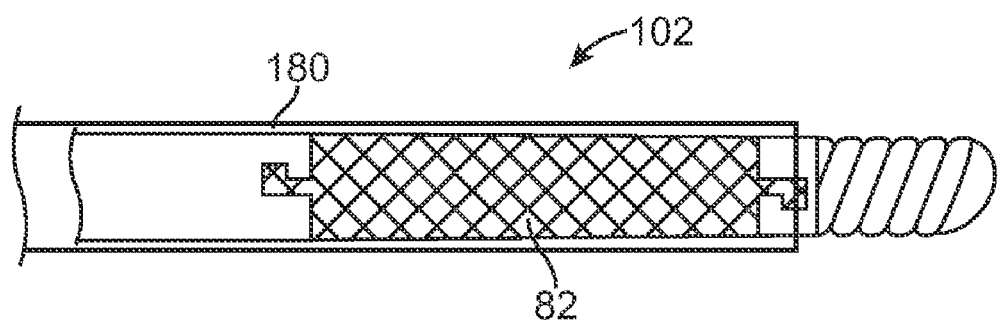
FIGS. 11A-11C illustrate an additional variation of an implant delivery system having a sleeve covering the stent.

FIG. 11A shows a detail view of the system 100 approach described in connection with FIG. 5 in which a stent 82 may be twisted to the reduced diameter configuration and covered with a sleeve 180 that is slidable over the stent at a distal end 102 of the system. With one or more sleeve portions covering a majority or substantially all of the stent, the stent need not be twisted down to the degree required for full compression without the sleeve.

Figure 11B:
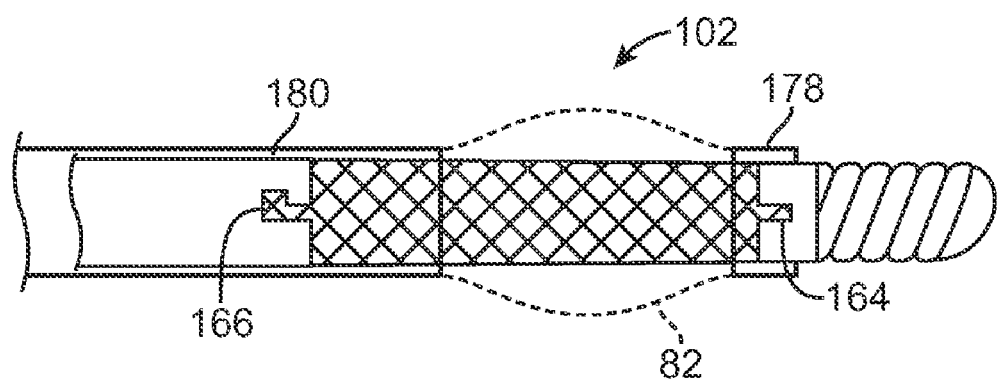
Figure 11C:
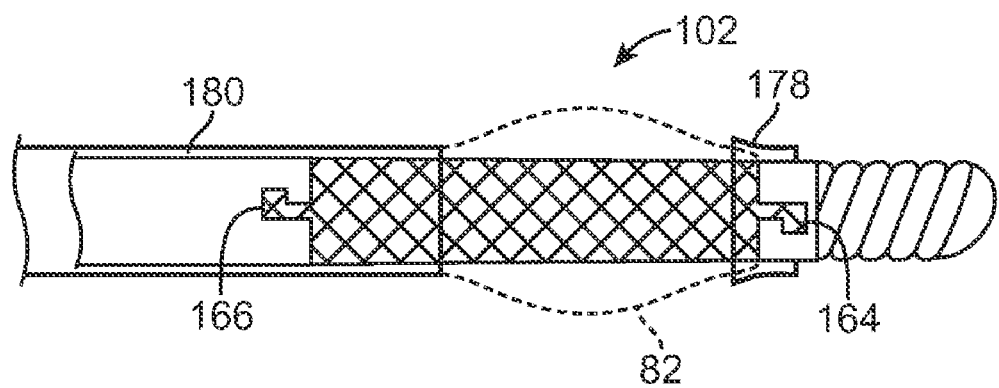

Each of FIGS. 11B and 11C illustrate approaches resembling those in FIGS. 10B and 9C, respectively. They differ primarily in that the FIG. 11B and 11C variations include a longer sleeve 180 that is relied upon, in part to maintain the compressed diameter of the stent. As shown in these figures, when sleeve 180 is withdrawn, stent 82 bulges outward. Such an approach may be employed to accomplish stent release without the need for any rotational manipulation of the delivery guide. Rather, by foreshortening the stent out of the far seats, the far side of the stent is able to self-release upon withdrawing sleeve 180.

In the alternative, delivery systems as shown in FIGS. 11A-11C may be employed more like simple-sheath systems. That is to say, twist imparted upon the stent may be imparted directly preceding insertion in the body or before sheath 180 withdrawal. In this manner, the twist imparted to the body may help break any stiction (static friction) and/or reduces the stent-induced-friction against the sleeve 180 by virtue of the twist to the stent body reducing the outward force the stent imparts on the sleeve. As such, the practitioner may then remove the sleeve 180 using less force.

In any case, FIG. 11B illustrates a variation in which an additional sleeve 178 is located over the far end of the stent 82 and where the far seat 164 allows for self-release of the stent 82. As the sleeve 180 withdraws from the stent 82, the stent 82 bulges or expands causing it to foreshorten and self-release from the far seat 164. It should be noted that the near end of the stent 82 may be designed to release the stent 82 upon removal of the sleeve 180. Alternatively, the near end of the stent 82 may release after the remainder of the stent 82 expands to a certain size that causes the near end to pull out of the near seat 166.

FIG. 11C illustrates a variation similar to that of FIGS. 11A and 11B in that the additional sleeve 178 is located over the stent 82. In this variation, the system includes an additional deformable sleeve 178. As the sleeve 180 withdraws from over the far end of the stent 82, the stent 82 bulges causing the deformable sleeve 178 to deform. This action allows the far end of the stent 82 to release from the far seats 164. As noted above, the near end of the stent 82 may be designed to release the stent 82 either upon removal of the sleeve 180. Alternatively, the near end of the stent 82 may release after the remainder of the stent 82 expands to a certain size that causes the near end to pull out of the near seat 166.

Figure 11D:
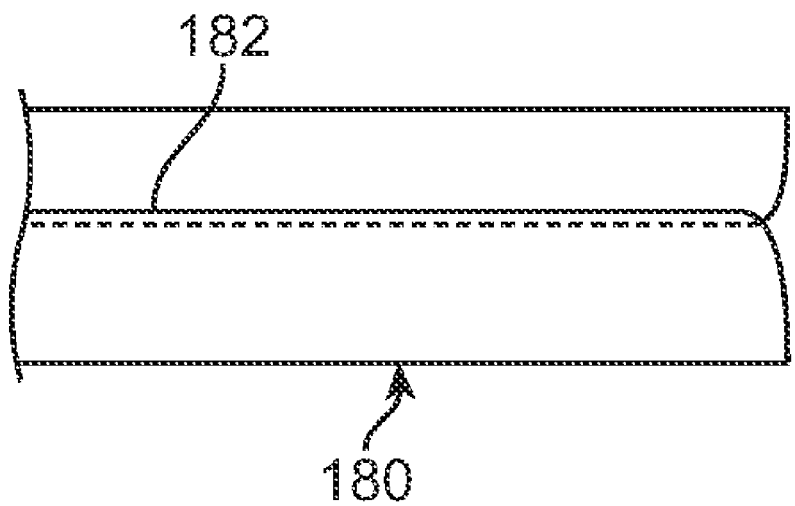
FIGS. 11D-11E illustrate variations of sleeves for use with the system.
Figure 11E:
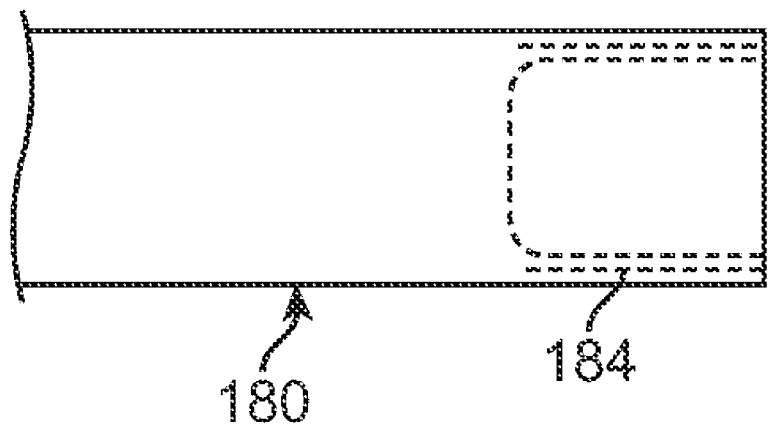

FIG. 11D illustrates a variation of a sleeve 180 for use with the systems such as described in FIGS. 11A-C. As shown, the sleeve 180 may be fabricated to include one or more wires or filaments 182 within or just beneath the sleeve wall. In practice, the medical practitioner pulls the wire/filament causing a tear in the sheath that allows (or causes) the stent to expand. In an alternative construction, the tear-wire 182 may be a suture strand or another filament that underlies the body and wraps around as shown. FIG. 11E illustrates another variation of a sleeve 180 including an everting portion 184 that folds upon itself. When subjected to the expansion force applied by the stent as it expands, the member may roll back. Such a construction may offer an alternative in instances above where a flexible sleeve 184 was called-out.

In another mode of operation, the everting portion 184 may evert when the sleeve 180 is withdrawn. As shown, the everting portion may comprise a plurality of separate members. Alternatively, sleeve 180 may be whole such that the outer sleeve portion and the everting portion roll past one another. Still further, it is contemplated that (especially for small-diameter delivery systems) that the everting portion tears open into individual segments as the near end of sleeve 180 is withdrawn. The material may be pre-scored or notched to facilitate such action as may be desirable for lowering forces or accommodating substantially inelastic material rolling from a smaller diameter to a relatively larger diameter.

Addition delivery system designs are shown in FIGS. 12A-14B. As in the other systems described herein, these delivery systems hold a radially-expandable prosthesis (such as a stent) in a collapsed configuration for delivery (at least in part) by winding-up or twisting the stent in a compressed profile. In certain of these examples, the stents include projections that nest within seats of the delivery system. In those variations in which the implant body does not include such projections, the delivery seats are adapted to interface directly with the stent.

Figure 12A:
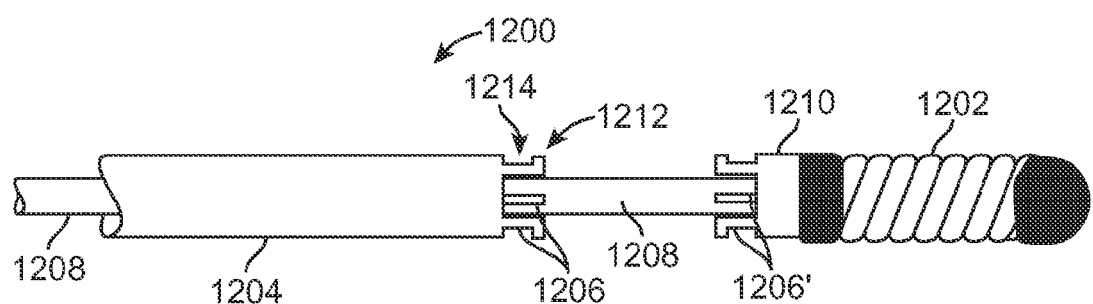
FIGS. 12A-12B show side views of an implant delivery system of the present invention in an unloaded and loaded configuration respectively.
Figure 12B:
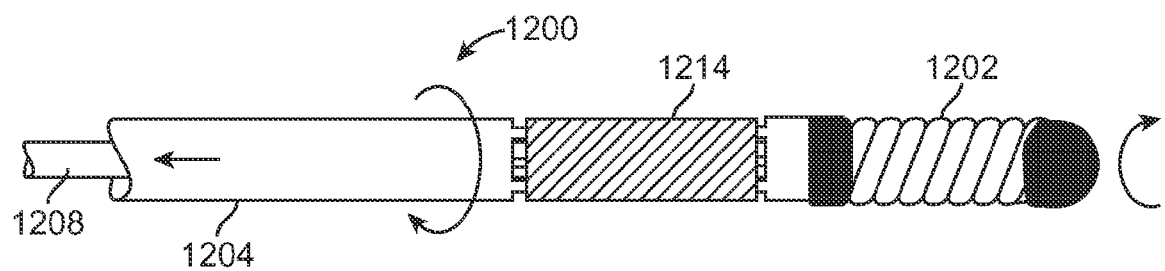

FIGS. 12A and 12B show a first variation of these devices in which projections from the stent may or may not be employed. As with the other variations of the invention above, delivery guide 182 preferably includes an atraumatic tip 1202. A body or shaft 1204 of the device in the form of a tube or sleeve includes hooks 1206 at a distal end. The body is advantageously made of hypotubing in order to manufacture the hooks integral thereto.

Near and far mating portions of the stent may be provided in openings within the cell structure or recesses formed within stent projections (see, e.g., FIGS. 8D and 8E) that accommodate the near and far seats of the delivery guide 1800. In this variation, the near seats comprise complementary seating hooks 1206' that are formed from the hypotubing. The hooks 1206' are distal to the hypotubing and supported by a core member 1208. Hooks 1206' may be formed in connection with a ring 1210 or be provided otherwise. In any case, the hooks (typically numbering at least two per side to balance forces) are dimensioned with a prong 1212 and recess 1214 suited for receipt of a stent. Together a complementary set of hooks 1206/1206' comprise the near and far seats that receive a stent and stretch it to hold it in a collapsed form when stretched or extended axially and twisted as shown in FIG. 12B. Alternatively, a twisting mode of stent compression or retention may alone be employed. Still, it has been appreciated that in certain loading schemes that a hook type interface (as shown in FIGS. 12A and 12B or as in FIGS. 6 and 7) can be very helpful.

Regardless, in the configuration shown where the hooks have no overhang (so as to facilitate stent release), the system relies on friction between the stent and hooks to hold the stent in place when the stent is axially stretched. Still, interference features between the stent and hooks may be provided to facilitate hold-down. Whatever the case, stent release is accomplished by releasing the tension and/or torque holding the stent in its collapsed profile.

Figure 13A:
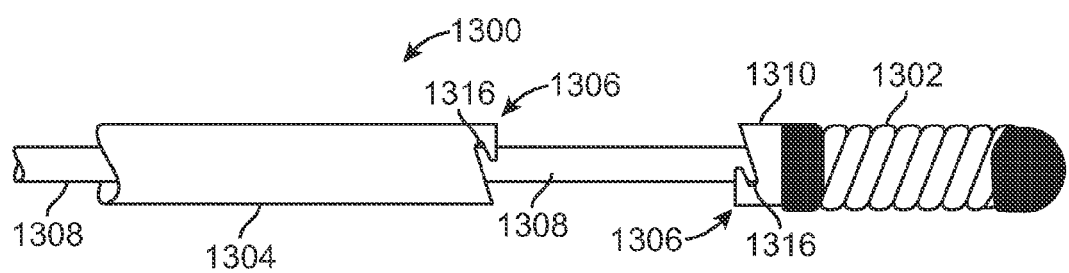
FIGS. 13A-13B shows another variation of an implant delivery system according to the principles of the present invention.
Figure 13B:
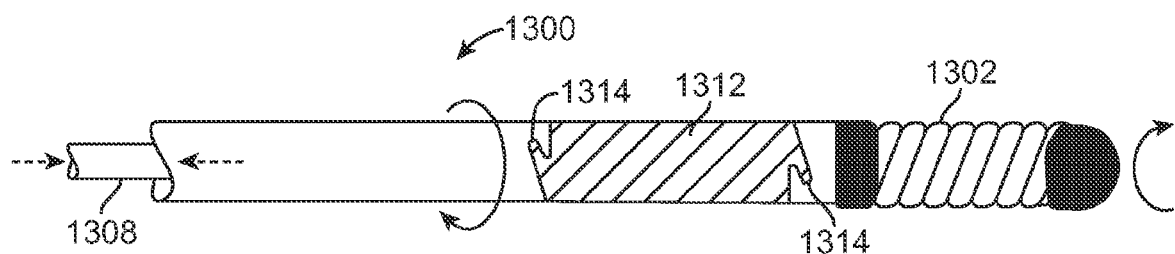

In the variation of the invention shown in FIGS. 13A and 13B, a delivery guide 1300 is provided that, again, preferably includes an atraumatic tip 1302. Furthermore, a body or shaft 1304 (advantageously, hypotubing) and a core wire member 1308 are provided. However, in the variation shown in FIGS. 13A and 13B, rather than providing radially-oriented hooks as seats, the near and far seats comprise radially oriented thread-like graspers 1306 and 1306'. At a proximal side of the device, they are shown integral with the hypotube. At a distal end, they are shown fabricated in connection with a ring 1310.

As shown in FIG. 13B, the graspers (ranging in number from at least one per side to very many) act like teeth capture a complimentarily shaped stent 1312 having mating portions or keys 1314 sized to fit within grasper slots 1316. By virtue of their complimentary angular component along which the stent projections and delivery guide components interface, these members are intended to "bite" like a threaded interface in order to reinforce their association. Otherwise, the current system differs little from that shown in FIGS. 6 and 7, relying on flag or flat hook-shaped members.

As in other one of the subject delivery systems, the stent is collapsed or at least held in collapsed state for delivery by imparting a torque to the system. In addition, the stent may be placed under tension as indicated—pushing the core wire forward relative to the hypotube (or vice versa). Naturally, release will be effected upon removal of the wind-up and/or pull-down forces. In which case, the stent will be able to expand and free its keys 1314 from slots 1314 by way of radial expansion.

Figure 14A:
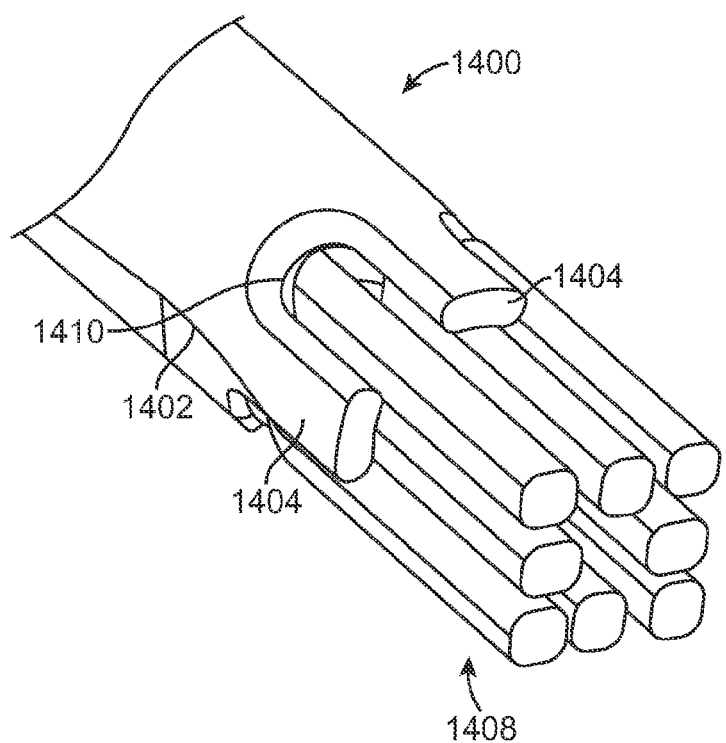
FIG. 14A is a partial sectional view of the end of a stent and corresponding features of a delivery guide interface.
Figure 14B:
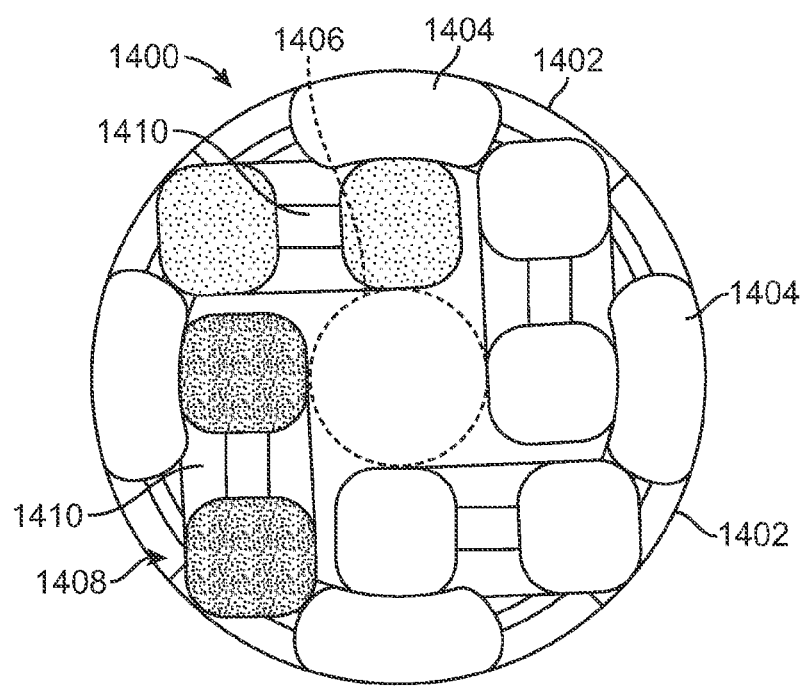
FIG. 14B is an end view of the members shown in FIG. 14A. Variation of the invention from the examples pictured is, of course, contemplated.

The final example of twist-based stent hold down provided herein is illustrated in FIGS. 14A and 14B. FIG. 14B shows a detail view of a delivery guide device seat in the form of a chuck-type 1400 feature comprising a body 1402 and a plurality of extensions 1404 therefrom. The body may be provided by hypotubing or a separate member. In any case, seat 1400 is shown riding over a core wire 1406 of a delivery device as with the hook or gasper features in the preceding variations of the invention.

The number of extension for the seat will depend on the stent 1408 with which the member is designed to interface. As shown in FIG. 14B, a four-extension chuck interface mates neatly with a stent having end portions that include four strut ends 1410. When closely-packed as shown, counter-rotation of complementary pairs of seats/chucks 1400 will capture the stent. Thus captured, the stent may be held down to a core member for delivery by this mode alone. In the alternative, some measure of tension, an overlaying sheath, or band, etc. may be applied thereto. Whatever the hold-down mode desired, it can be appreciated that the system of FIGS. 14A and 14B represents a sort of "self-locking" system, just as other ones of those described above.

In more general terms, the invention includes methods that may be performed using the subject devices or by other means. The methods may all comprise the act of providing a suitable device. Such provision may be performed by the end user. In other words, the "providing" (e.g., a delivery system) merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally know or appreciated by those with skill in the art. For example, one with skill in the art will appreciate that a lubricious coating (e.g., hydrophilic polymers such as polyvinylpyrrolidone-based compositions, fluoropolymers such as tetrafluoroethylene, hydrophilic gel or silicones) may be placed on the core member of the device, if desired to facilitate low friction manipulation. The same may hold true with respect to method-based aspects of the invention in terms of additional acts as commonly or logically employed.

In addition, though the invention has been described in reference to several examples, optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in the appended claims, the singular forms "a," "an," "said," and "the" include plural referents unless the specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth n the claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of the claim language.

That being said, we claim:

1. A system for treating a body organ, the system comprising:
    an elongate member having a distal portion;
    a prosthesis comprising a near end, a far end and a structure extending therebetween, where the structure comprises a mesh, lattice, or woven structure having an untwisted configuration and a twisted reduced diameter configuration after rotation of the near and far ends relative to one another in a first direction, the prosthesis further comprising a plurality of near mating portions comprising a plurality of projections extending from one of said ends of said prosthesis and a plurality of far mating portions comprising a plurality of projections extending from the other one of said ends of said prosthesis, the prosthesis structure being in said twisted reduced diameter configuration and releaseably mounted on said elongate member through said near and far mating portions; and
    a near seat receiving the near mating portions of the prosthesis and a far seat receiving the far mating portions of the prosthesis, said near and far seats being coupled to said elongate member, wherein the near and far mating portions of the prosthesis are nested with the near and far seats such that the near and far ends of the prosthesis are restrained from rotating in a second direction to maintain the prosthesis structure in said twisted reduced diameter configuration.

2. The system of claim 1, wherein the near seat and near mating portion comprise a near retaining means for retaining the near end of the prosthesis to the elongate member, and wherein the far seat and far mating portion comprise a far retaining means for retaining the far end of the prosthesis to the elongate member.

3. The system of claim 1, wherein the near and far seats each comprise a respective geometry shaped to receive the near and far mating portions respectively.

4. The system of claim 3, where the near seat geometry is selected from "L" shape, "T" shape, "V" shape, "C" shape, circular, rectangular, square, polygonal, triangular and elongate forms.

5. The system of claim 3, where the far seat geometry is selected from "L" shape, "T" shape, "V" shape, "C" shape, circular, rectangular, square, polygonal, triangular and elongate forms.

6. The system of claim 3, where the near mating portions comprises a plurality of hook shaped members.

7. The system of claim 6, where the near seat geometry comprises an opening shaped to receive a portion of the hook shaped member.

8. The system of claim 3, where the far mating portions comprises a plurality of hook shaped members.

9. The system of claim 8, where the near seat geometry comprises an opening shaped to receive a portion of a hook shaped member.

10. The system of claim 1, where the near seat and far seat are attached to the elongate member.

11. The system of claim 10, where the elongate member further comprises an inner member and an outer member having a distal end.

12. The system of claim 11, where the inner member extends through at least a portion of the outer member and out through the distal end of the outer member, and where the inner member is moveable relative to the distal end of the outer member.

13. The system of claim 12, where the outer member comprises a radiopaque marker.

14. The system of claim 12, where outer member includes the near seat and the inner member includes the far seat.

15. The system of claim 12, where the inner member and outer member are axially moveable relative to one another.

16. The system of claim 12, where the inner member and outer member are rotatable relative to one another.

17. The system of claim 16, where the near seat and far seat are releasably lockable to control rotation of the near seat relative to the far seat.

18. The system of claim 12, where the prosthesis is mounted about a distal portion of the inner member and adjacent to the distal end of the outer member.

19. The system of claim 11, where the outer member is slidably located over at least the near seat.

20. The system of claim 11, where the outer member further comprises a wire or filament located in a wall of the outer member, such that when pulled, the wire or filament tears the outer member.

21. The system of claim 11, where the outer member further comprises an end portion configured to evert.

22. The system of claim 1, where the prosthesis comprises a stent.

23. The system of claim 22, where an Af temperature of the stent is set for a shape memory.

24. The system of claim 23, where the Af temperature of the stent is set for super-elasticity.

25. The system of claim 22, where the stent is a self-expanding stent.

26. The system of claim 22, where the stent further comprises a therapeutic agent.

27. The system of claim 22, where the stent further comprises a radiopaque marker.

28. The system of claim 1, where the elongate member further comprises a radiopaque marker.

29. The system of claim 1, further comprising a first sleeve located over at least the near seat.

30. The system of claim 29, where the first sleeve is flexible.

31. The system of claim 1, further comprising a second sleeve located over at least the far seat.

32. The system of claim 31, where the second sleeve is flexible.

33. The system of claim 1, wherein said elongate member is adapted to be passed through vasculature.

34. The system of claim 1, wherein said elongate member is a guide wire.

35. The system of claim 1, wherein said far seat is axially moveable relative to the near seat.

36. The system of claim 1, wherein said far seat is rotatable relative to the near seat.

37. The system of claim 36, wherein said elongate member is a guide wire.

38. The system of claim 1, wherein said structure comprises a lattice of closed cells.

39. The system of claim 38, wherein each closed cell comprises a plurality of struts including a first pair of axially adjacent and interconnected struts and a second pair of axially adjacent and interconnected struts, one strut of the first pair being directly connected to the one strut of the second pair through a strut junction.

40. The system of claim 38, wherein each closed cell consists of four interconnected struts.

41. A system for treating a body organ, the system comprising:
   an elongate member having a distal portion;
   a prosthesis comprising a near end, a far end and a structure extending therebetween, where the structure comprises a mesh, lattice, or woven structure having an untwisted configuration and a twisted reduced diameter configuration after rotation of the near and far ends relative to one another in a first direction, the prosthesis further comprising near mating portions and far mating portions, the prosthesis structure being in said twisted reduced diameter configuration and releaseably mounted on said elongate member through said near and far mating portions; and
   a near seat receiving the near mating portions of the prosthesis and a far seat receiving the far mating portions of the prosthesis, said near and far seats being coupled to said elongate member, wherein the near and far mating portions of the prosthesis are nested with the near and far seats such that the near and far ends of the prosthesis are restrained from rotating in a second direction to maintain the prosthesis structure in said twisted reduced diameter configuration;
   wherein the near and far seats each comprise a respective geometry shaped to receive the near and far mating portions respectively; and wherein the near mating portions of the prosthesis comprises a plurality of near projections and the far mating portions of the prosthesis comprises a plurality of far projections, wherein the near projections extend from the near end of the prosthesis and the far projections extend from the far end of the prosthesis, and wherein the near seat geometry comprises a plurality of openings shaped to receive at least one of the near projections and wherein the far seat geometry comprises a plurality of openings shaped to receive at least one of the far projections.

42. The system of claim 41, where each of the plurality of near seat openings comprises an elongate opening.

43. The system of claim 41, where the plurality of near seat openings comprises a plurality of pockets.

44. The system of claim 41, where each of the plurality of far seat openings comprises an elongate opening.

45. The system of claim 41, where the plurality of far seat openings comprises a plurality of pockets.

46. A stent delivery system comprising:
an elongate stent delivery member having a proximal end and a distal end, said elongate stent delivery member adapted for manipulation through vasculature;
a self-expanding non-coil type stent comprising a plurality of closed cells and having a first end, a second end, and structure extending between said first and second ends, said self-expanding stent being twistable from an untwisted tubular configuration where a portion of the stent has a first diameter and said first and second ends have a first relative position to a twisted configuration upon rotation of at least one of said stent ends relative to the other to change said first relative position of said first and second stent ends and to reduce the diameter of said portion of said stent, said self-expanding stent surrounding a portion of said elongate member and being releasably secured thereto while being maintained in said twisted configuration.

47. The stent delivery system of claim 46, wherein said stent structure comprises a plurality of struts that define a lattice of closed cells.

48. The stent delivery system of claim 47, wherein each closed cell comprises a plurality of struts including a first pair of axially adjacent and interconnected struts and a second pair of axially adjacent and interconnected struts, one strut of the first pair being directly connected to the one strut of the second pair through a strut junction.

49. The stent delivery system of claim 47, wherein each closed cell consists of four interconnected struts.

50. The stent delivery system of claim 46, further including a first seat rotatably coupled to said elongate member, wherein said stent includes a first plurality of projections and one of said stent ends is secured to said first seat through said first plurality of projections.

51. The stent delivery system of claim 50, further including a second seat coupled to said elongate member, wherein said stent includes a second plurality of projections and the other one of said stent ends being secured to said second seat through said second plurality of projections.

52. The stent delivery system of claim 51, wherein said second seat is integral with said elongate member.

53. The stent delivery system of claim 51, wherein said second seat is affixed to said elongate member.

54. The stent delivery system of claim 50, wherein said first seat and elongate member are axially movable relative to one another.

55. The stent delivery system of claim 46, further including a first seat coupled to said elongate member and to which one of said stent ends is secured and a second seat coupled to said elongate member and to which the other of said stent ends is secured, said first seat and elongate member being axially movable relative to one another.

56. The stent delivery system of claim 46, further including a first seat coupled to said elongate member, wherein said stent includes a first and second plurality of projections with one of said stent ends being secured to said elongate member through said first plurality of projections and further including a second seat coupled to said elongate member with the other one of said stent ends being secured thereto through said second plurality of projections.

57. The stent delivery system of claim 56, wherein one of said seats is axially moveable relative to the other of said seats.

58. The stent delivery system of claim 57, wherein one of said seats is rotatable relative to the other of said seats.

59. The stent delivery system of claim 56, wherein one of said seats is rotatable relative to the other of said seats.

60. The stent delivery system of claim 56, further including a first member surrounding at least a portion of said stent and first seat and a second member surrounding at least a portion of said stent and said second seat.

61. The stent delivery system of claim 60, wherein at least one of said first and second members comprises a sleeve.

62. The stent delivery system of claim 46, wherein said elongate member comprises a guide wire.

63. A stent delivery system comprising:
an elongate stent delivery member having a proximal end and a distal end, said elongate stent delivery member adapted for manipulation through vasculature; and
a self-expanding non-coil type stent comprising a plurality of closed cells, said self-expanding stent having an untwisted tubular configuration and a twisted configuration where the stent is under torsion and has a reduced profile, said stent being releasably secured to said elongate stent delivery member in said twisted reduced profile configuration.

64. The system of claim 63, wherein said elongate stent delivery member comprises a guide wire.

65. The system of claim 63, wherein said stent comprises a plurality of struts that define a lattice of closed cells.

66. The system of claim 65, wherein each closed cell comprises a plurality of struts including a first pair of axially adjacent and interconnected struts and a second pair of axially adjacent and interconnected struts, one strut of the first pair being directly connected to the one strut of the second pair through a strut junction.

67. The system of claim 65, wherein each closed cell consists of four interconnected struts.

68. The system of claim 63, further including first and second seats coupled to said elongate stent delivery member, said stent having portions in said first seat and portions in said second seat.

69. The system of claim 63, further including first and second seats coupled to said elongate stent delivery member, said stent having a plurality of axially extending discrete projections seated in said first seat and a plurality of axially extending discrete projections seated in said second seat.

70. The system of claim 69, wherein one of said seats is rotatably coupled to said elongate stent delivery member.

* * * * *